United States Patent
Ozoe et al.

(10) Patent No.: US 9,505,713 B2
(45) Date of Patent: Nov. 29, 2016

(54) HIGH-PURITY SODIUM P-STYRENESULFONATE WITH EXCELLENT HUE, METHOD FOR PRODUCING THE SAME, POLY(SODIUM P-STYRENESULFONATE) WITH EXCELLENT HUE USING THE SAME, AND DISPERSANT AND SYNTHETIC STARCH FOR CLOTHING FINISHING USING THE POLY(SODIUM P-STYRENESULFONATE)

(71) Applicant: TOSOH ORGANIC CHEMICAL CO., LTD., Yamaguchi (JP)

(72) Inventors: Shinji Ozoe, Yamaguchi (JP); Kenichi Yamanoi, Yamaguchi (JP); Hideaki Matsunaga, Yamaguchi (JP)

(73) Assignee: TOSOH ORGANIC CHEMICAL CO., LTD, Shunan-Shi, Yamaguchi (JP)

( * ) Notice: Subject to any disclaimer, the term of this patent is extended or adjusted under 35 U.S.C. 154(b) by 0 days.

(21) Appl. No.: 14/432,049

(22) PCT Filed: Sep. 2, 2013

(86) PCT No.: PCT/JP2013/073503
§ 371 (c)(1),
(2) Date: Mar. 27, 2015

(87) PCT Pub. No.: WO2014/061357
PCT Pub. Date: Apr. 24, 2014

(65) Prior Publication Data
US 2015/0246876 A1    Sep. 3, 2015

(30) Foreign Application Priority Data

Oct. 15, 2012 (JP) .................. 2012-227996
Oct. 16, 2012 (JP) .................. 2012-229151

(51) Int. Cl.
| | | |
|---|---|---|
| C07C 309/00 | (2006.01) | |
| C07C 309/30 | (2006.01) | |
| C07C 303/32 | (2006.01) | |
| C08F 12/30 | (2006.01) | |
| D06M 15/233 | (2006.01) | |
| C07C 303/44 | (2006.01) | |
| C08F 212/14 | (2006.01) | |
| D06M 15/356 | (2006.01) | |

(52) U.S. Cl.
CPC ........... C07C 309/30 (2013.01); C07C 303/32 (2013.01); C07C 303/44 (2013.01); C08F 12/30 (2013.01); C08F 212/14 (2013.01); D06M 15/233 (2013.01); D06M 15/3566 (2013.01)

(58) Field of Classification Search
CPC . C07C 303/32; C07C 309/29; C07C 303/44; C07C 309/30; C08F 212/14; C08F 12/30; C08F 220/06; D06M 15/233; D06M 15/3566; A61H 2201/5025; A61H 7/005; A61H 7/007
See application file for complete search history.

(56) References Cited

U.S. PATENT DOCUMENTS

| | | | | |
|---|---|---|---|---|
| 3,939,130 A | * | 2/1976 | Ponticello | ............... C08F 12/22 430/503 |
| 5,898,083 A | * | 4/1999 | Matsunaga | ........... C07C 309/30 562/87 |
| 2015/0246876 A1 | | 9/2015 | Ozoe et al. | |

FOREIGN PATENT DOCUMENTS

| | | |
|---|---|---|
| JP | 52-23038 A | 2/1977 |
| JP | 55-31059 A | 3/1980 |
| JP | 03-168239 A | 7/1991 |
| JP | 5-239774 A | 9/1993 |
| JP | 10-152465 A | 6/1998 |
| JP | 10-182591 A | 7/1998 |
| JP | 11-181004 A | 7/1999 |
| JP | 2005-263608 A | 9/2005 |
| JP | 2014-80505 A | 5/2014 |
| JP | 49-95940 | 6/2016 |
| WO | 2013/073259 A1 | 5/2013 |

OTHER PUBLICATIONS

'239 (JP03-168239, 1991) translated.*
591' (JP10-182591 1998) Translated.*
International Search Report for PCT/JP2013/073503 dated Nov. 12, 2013 [PCT/ISA/210].
Written Opinion for PCT/JP2013/073503 dated Nov. 12, 2013 [PCT/ISA/237].
International Preliminary Report on Patentability issued in application No. PCT/JP2013/073503 dated Apr. 30, 2015.
English Translation of International Preliminary Report on Patentability issued in Application No. PCT/JP2013/073503 dated Apr. 30, 2015.

* cited by examiner

*Primary Examiner* — Yevegeny Valenrod
*Assistant Examiner* — Blaine G Doletski
(74) *Attorney, Agent, or Firm* — Sughrue Mion, PLLC

(57) ABSTRACT

Provided are high purity sodium p-styrenesulfonate with an excellent hue which is useful as a reactive emulsifier or dispersant for producing a polymer emulsion, or synthetic starch for clothing ironing and poly(sodium p-styrene-sulfonate) with an excellent hue using the same or sodium p-styrenesulfonate improved in fluidity while keeping good solubility.
An aqueous p-β-bromoethylbenzenesulfonic acid solution and an aqueous sodium hydroxide solution are reacted under specific conditions to control the particle size, thereby obtaining sodium p-styrenesulfonate particles improved in a balance between fluidity and solubility, and further, impurities such as isomers are reduced, thereby obtaining high-purity sodium p-styrenesulfonate with an excellent hue.

11 Claims, 5 Drawing Sheets

HIGH-PURITY SODIUM P-STYRENESULFONATE WITH EXCELLENT HUE, METHOD FOR PRODUCING THE SAME, POLY(SODIUM P-STYRENESULFONATE) WITH EXCELLENT HUE USING THE SAME, AND DISPERSANT AND SYNTHETIC STARCH FOR CLOTHING FINISHING USING THE POLY(SODIUM P-STYRENESULFONATE)

CROSS REFERENCE TO RELATED APPLICATIONS

This application is a National Stage of International Application No. PCT/JP2013/073503 filed Sep. 2, 2013, claiming priorities based on Japanese Patent Application Nos. 2012-227996 filed Oct. 15, 2012 and 2012-229151 filed Oct. 16, 2012, the contents of all of which are incorporated herein by reference in their entirety.

TECHNICAL FIELD

The present invention relates to high-purity sodium p-styrenesulfonate with an excellent hue, a method for producing the same, poly(sodium p-styrenesulfonate) with an excellent hue using the same, and a dispersant and synthetic starch for clothing finishing using the poly(sodium p-styrenesulfonate).

Further, the present invention relates to sodium p-styrenesulfonate also with excellent fluidity and solubility, and a method for producing the same. That is to say, the present invention relates to sodium p-styrene-sulfonate with excellent fluidity and solubility, which is sodium p-styrenesulfonate with an appropriate particle size and a low water content, and a method for producing the same.

BACKGROUND ART

A p-styrenesulfonic acid (salt) represented by sodium p-styrenesulfonate is a functional monomer having a radical polymerizable vinyl group, a hydrophobic benzene ring having π electrons, and a sulfonic acid (salt) group that is a strong electrolyte, and has been valued in various industrial fields. For example, it has been used as a reactive emulsifier in order to improve stability of an emulsion and water resistance or cationic dye dyeability of a (emulsion) polymer. Further, a polymer or a copolymer of sodium p-styrenesulfonate has been used as a dispersant for producing various aqueous dispersions of pigments, antioxidants, various polymers (tackifier resins, chloroprene rubber, polyacrylic acid esters, polyesters, styrene-butadiene copolymers, polyvinyl chloride, poly-acrylonitrile, polysilicones, conductive polymers and the like), nanocarbon materials, silica particles for hot forging release agents or abrasives, battery electrode materials (carbon, lithium iron phosphate, lithium manganese phosphate and the like), photographic silver halides and the like. Furthermore, the polymer of sodium p-styrenesulfonate has been utilized as synthetic starch for clothing finishing such as an ironing agent, a hair care product, an antistatic agent, a resist acid generator, a water treatment agent, an allergen scavenger, an ion-exchange resin, a plating solution additive, a detergent for production of semiconductors and hard disks, an additive to fluids for shale oil drilling and a flame retardant for resins.

In the above-mentioned application fields, various improvements have been required for sodium p-styrenesulfonate and the (co)polymer thereof. Among these, an improvement need common to many uses is hue. The hue of sodium p-styrenesulfonate and the (co)polymer thereof is an important factor directly exerting an effect on the commercial value, particularly in uses of an adhesive, a polymer emulsion for pigments, synthetic starch for clothing finishing such as an ironing agent, an antistatic agent, a frame retardant for transparent resins, a photographic silver halide emulsion and the like. That is to say, conventional sodium p-styrenesulfonate industrially available and the (co)polymer thereof exhibit a pale yellow to pale yellowish brown color, and it has been strongly desired to make them light-colored or colorless.

About the hue of sodium p-styrenesulfonate, an influence of impurities is suggested (for example, Patent Document 1). However, about the most important impurities, metal halides are only mentioned, and no other specific hue is mentioned in any way. Further, about the hue of the (co)polymer of sodium p-styrenesulfonate, an influence of a polymerization initiator is suggested (for example, Patent Document 2). However, iron and other impurities contained in sodium p-styrenesulfonate as a raw material and an influence thereof on the hue are not mentioned in any way.

Further, chloroprene rubber-based adhesives have long been used as all-purpose adhesives. Methods for producing chloroprene rubber are publicly known. For example, chloroprene or chloroprene and a radical polymerizable monomer copolymerizable therewith are emulsified in water using an alkali metal salt of disproportionated rosin acid (acting as an emulsifier) and an alkali metal salt of a naphthalenesulfonic acid formalin condensate (acting as a dispersant), and a radical polymerization initiator is added thereto to perform emulsion polymerization. The unreacted monomer(s) in a chloroprene rubber emulsion obtained is removed by a steam distillation process. Finally, chloroprene rubber is taken out of the emulsion by a process such as freezing coagulation, and washed with water and dried, thereby being able to produce solid chloroprene rubber (for example, Non-Patent Document 1). The chloroprene rubber-based adhesive is produced by dissolving the above-mentioned chloroprene rubber and compounding agents such as a tackifier resin, a metal oxide and a crosslinking agent in an organic solvent such as toluene, methylcyclohexane, n-hexane, methyl ethyl ketone or an acetate ester. When the chloroprene rubber-based adhesives are used for production of footwear or sporting goods, an excellent hue (to be as close to colorless as possible) is required.

Accordingly, as a method for improving the hue of the adhesives, there has been proposed a method using as a dispersant an alkali metal salt of a styrenesulfonic acid (co)polymer that is hardly discolored, instead of the above-mentioned alkali metal salt of the naphthalenesulfonic acid formalin condensate (for example, Patent Document 3). Surely, the hue is improved. However, it is not necessarily satisfactory, and a further improvement has been required. Further, the hue of the poly(sodium p-styrenesulfonate) (co)polymer used is not mentioned in any way.

Furthermore, as synthetic starch used for a clothing finishing agent such as an ironing agent, there has been known poly(Sodium p-styrenesulfonate) (Patent Document 4). The hue is extremely important in this use, and it has been required to make the synthetic starch more colorless. However, the hue of poly(sodium p-styrenesulfonate) is not mentioned in any way.

On the other hand, it has previously been known that sodium p-styrenesulfonate can be produced by the reaction of p-β-bromoethylbenzenesulfonic acid and sodium hydroxide (see Patent Documents 5 and 6).

Patent Document 5 describes a method for producing a hemihydrate of sodium p-styrenesulfonate by charging a reactor with an aqueous sodium hydroxide solution containing a slight amount of sodium nitrite as a polymerization inhibitor under a nitrogen atmosphere, performing the reaction at 90° C. while adding dropwise p-β-bromoethylbenzenesulfonic acid thereto to obtain crystals of sodium p-styrenesulfonate, and thereafter performing cooling, centrifugal filtration and forced fluidization. It is only described that the particle size of sodium p-styrenesulfonate is usually from several micrometers to several millimeters, and no observed value is described. It is assumed to have a particle size equivalent to that of one on the market at present, that is to say, a median diameter of about 20 μm. Further, the relationship among the particle size, water content, solubility and fluidity is not mentioned in any way.

Patent Document 6 describes a method for producing a hemihydrate of sodium p-styrenesulfonate by performing the reaction at 90° C. while concurrently feeding an aqueous sodium hydroxide solution containing a small amount of sodium nitrite as a polymerization inhibitor and p-bromoethylbenzenesulfonic acid to a reactor, continuously taking out a sodium p-styrenesulfonate crystal slurry formed, and performing centrifugal filtration and forced fluidization. It is described that the shape of sodium p-styrenesulfonate is scale-like and that the observed value of particle size is from 160 μm to 760 μm. Further, similarly to Patent Document 5, the relationship among the particle size, water content, solubility and fluidity is not mentioned in any way.

However, conventional sodium p-styrenesulfonate having a median diameter of less than 25 μm has had a problem with handling properties, such as the occurrence of clogging in a charging hopper at the time when used in large amounts in a plant. That is to say, it has been lacking in fluidity as a powder. On the other hand, when the median diameter of sodium p-styrenesulfonate exceeds 150 μm, the rate of dissolution in water has decreased at the time when used in a plant to cause a problem such as clogging of a strainer, although satisfactory in fluidity. That is to say, sodium p-styrenesulfonate improved in fluidity without impairing the solubility of sodium p-styrenesulfonate has been required.

Further, in the above-mentioned detergents for production of semiconductors and hard disks, antistatic agents of films for electronic materials, dispersants for conductive polymers, photographic silver halide emulsifiers and the like, particularly in electronic material uses, it has recently been required to decrease impurities such as sodium bromide contained in p-styrenesulfonic acid (salts) and p-styrenesulfonic acid (salt) polymers, nuclear bromides of p-β-bromoethylbenzenesulfonic acid and p-styrenesulfonic acid, and excess metals and bromine components. It has been known that the impurities such as sodium bromide can be decreased by washing or recrystallization with an aqueous solvent (for example, Patent Document 7). Although the purity is described in Patent Document 7, the contents of alkali metal halides are not clear, and there is no description for the other impurities at all. Further, an effect of the particle size of sodium p-styrenesulfonate before purification on the purification efficiency, namely the purity after purification, is not mentioned in any way.

PRIOR-ART DOCUMENTS

Patent Documents

[Patent Document 1] JP-A-51-138645
[Patent Document 2] JP-A-11-181004
[Patent Document 3] Japanese Patent No. 3601136
[Patent Document 4] Japanese Patent No. 2808205
[Patent Document 5] Japanese Patent No. 3601222
[Patent Document 6] Japanese Patent No. 3890642
[Patent Document 7] JP-B-58-22477

Non-Patent Documents

[Non-Patent Document 1] Technology of Adhesion, Vol. 21, No. 4, pp. 14 to 19, 2002, published by Adhesion Society of Japan

OUTLINE OF THE INVENTION

Problems that the Invention is to Solve

The present invention has been made in view of the above-mentioned problems, and an object thereof is to provide high-purity sodium p-styrenesulfonate and a sodium styrenesulfonate (co)polymer (hereinafter also referred to as "sodium PSS" or "Poly(Sodium p-Styrenesulfonate)") with an excellent hue, which are useful for producing a polymer emulsion such as chloroprene rubber or synthetic starch for clothing finishing with an excellent hue.

Further, the present invention provides a powder (particles) of sodium p-styrenesulfonate with excellent fluidity and solubility, which has a median diameter of 25.00 to 150.00 μm and a content of small particles less than 10.00 μm of 10.00% or less.

Means for Solving the Problems

The present inventors have made intensive studies in order to solve the above-mentioned problems. As a result, it has been found that high-purity sodium p-styrenesulfonate decreased in iron and specific impurities and a sodium p-styrenesulfonate (co)polymer produced using the same have an extremely excellent hue, and become sodium p-styrenesulfonate and sodium PSS useful for producing a polymer emulsion such as chloroprene rubber or synthetic starch for clothing finishing, thus leading to completion of the present invention.

Further, the present inventors have made intensive studies in order to solve the above-mentioned problem. As a result, it has been found that sodium p-styrenesulfonate having a median diameter of 25.00 to 150.00 μm and a content of small particles less than 10.00 μm of 10.00% or less, which is produced under specific conditions, is excellent in a balance between fluidity and solubility, and further, can be extremely efficiently purified, when the sodium p-styrenesulfonate is purified using an aqueous solvent to increase the purity thereof, thus leading to completion of the present invention.

The present invention relates to high-purity sodium p-styrenesulfonate with an excellent hue (hereinafter also referred to as "high-purity sodium p-styrenesulfonate"), in which the iron content in sodium p-styrenesulfonate is less than 3.00 μg/g, the sodium bromide content is less than 2.50 wt %, and the peak area ratios of (a) sodium o-styrenesulfonate, (b) sodium p-β-bromoethylbenzenesulfonate, (c) sodium m-styrene-sulfonate, (d) sodium bromostyrenesulfonate and (e) sodium p-β-hydroxyethylbenzenesulfonate, which are determined by high-performance liquid chromatography (HPLC), are (a) ≤0.40%, (b) ≤4.00%, (c) ≤8.00%, (d) ≤0.10% and (e) ≤0.80%, respectively (provided that the sum of peak areas of sodium p-styrenesulfonate and (a) to (e) is 100).

Here, in high-purity sodium p-styrenesulfonate with an excellent hue of the present invention, more preferably, the iron content in sodium p-styrenesulfonate is less than 3.00 μg/g, the sodium bromide content is less than 2.50 wt %, and the peak area ratios of (a) sodium o-styrenesulfonate, (b) sodium p-β-bromoethylbenzenesulfonate, (c) sodium m-styrenesulfonate, (d) sodium bromostyrenesulfonate and (e) sodium p-β-hydroxyethylbenzenesulfonate, which are determined by high-performance liquid chromatography (hereinafter referred to as HPLC), are (a) ≤0.20%, (b) ≤0.50%, (c) ≤3.00%, (d) ≤0.10% and (e) ≤0.20%, respectively (provided that the sum of peak areas of sodium p-styrenesulfonate and (a) to (e) is 100).

Further, preferably, high-purity sodium p-styrenesulfonate of the present invention is composed of particles having a median diameter measured with a laser diffraction/scattering particle size analyzer of 25.00 to 150.00 μm and a content of small particles less than 10.00 μm of 10.00% or less, and has a water content of 10.00 wt % or less and a repose angle of 55 degrees or less.

More preferably, high-purity sodium p-styrenesulfonate of the present invention is composed of particles having a median diameter measured with a laser diffraction/scattering particle size analyzer of 40.00 to 90.00 μm and a content of small particles less than 10.00 μm of 3.00% or less, and has a water content of 8.00 wt % or less and a repose angle of 50 degrees or less.

High-purity sodium p-styrenesulfonate described above preferably has a sodium bromide content of 0.20 wt % or less.

Then, the present invention relates to a method for producing high-purity sodium p-styrenesulfonate with excellent fluidity and solubility comprising concurrently feeding sodium hydroxide and β-bromoethylbenzenesulfonic acid to a reaction tank at a constant rate, wherein reaction crystallization is performed at 60 to 110° C. for 1 to 7 hours, while performing control so as to keep the sodium hydroxide concentration in the reaction tank [(the weight of total sodium hydroxide fed/the weight of the total reaction solution in the reaction tank)×100] at 10.00 to 20.00 wt % and so as to increase the p-β-bromoethylbenzenesulfonic acid concentration [(the weight of total p-β-bromoethylbenzenesulfonic acid fed/the weight of the total reaction solution in the reaction tank)×100] from 0.00 wt % to 30.00 to 50.00 wt % over 1 to 7 hours, and a wet cake obtained by solid-liquid separation is forcedly fluidized.

Next, the present invention relates to poly(Sodium p-styrenesulfonate) with an excellent hue having the following repeating structural unit A or the following repeating structural unit A and the following repeating structural unit B, which is produced using high-purity sodium p-styrenesulfonate described above.

[Chemical Formula 1]

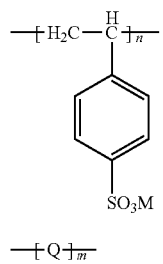

[in the repeating structural units A and B, M represents a sodium cation, Q represents a radical polymerizable monomer residue, n represents an integer of 1 or more, and m represents an integer of 0 or more.]

Here, sodium PSS of the present invention preferably has a weight average molecular weight determined by gel permeation chromatography (hereinafter referred to as GPC) of 2,000 to 1,000,000.

Further, Q in the above-mentioned repeating structural unit B is preferably at least one radical polymerizable monomer residue selected from the group consisting of a (meth)acrylic acid residue, a (meth)acrylic acid ester residue, a maleic anhydride residue, a maleic acid residue, a maleimide residue, a (meth)acrylamide residue, a styrene residue and a styrene derivative residue.

Then, the present invention relates to a dispersant comprising sodium PSS described above as an effective ingredient, or a clothing ironing agent produced using sodium PSS as synthetic starch.

Advantageous Effects of the Invention

High-purity sodium p-styrenesulfonate of the present invention and the sodium p-styrenesulfonate (co)polymer produced using the same have excellent hues because their contents of iron and other impurities are small, and are useful for improving the hues of various aqueous dispersions such as chloroprene rubber and synthetic starch for clothing finishing.

Further, according to the present invention, there is provided sodium p-styrenesulfonate improved in fluidity that has been the conventional problem, while keeping good solubility, by controlling the particle size. Furthermore, sodium p-styrenesulfonate of the present invention having the controlled particle size is excellent in purification efficiency, at the time when the purity is increased by recrystallization purification or the like.

BRIEF DESCRIPTION OF THE DRAWINGS

In FIG. 1, the ordinate shows the peak intensity (the absorption intensity of a detector, the unit is arbitrary), and the abscissa shows the elution time (the unit is minutes). (a), (b), (c), (d) and (e) in FIG. 1 show the intensity of (a) sodium o-styrenesulfonate, (b) sodium p-β-bromoethylbenzenesulfonate, (c) sodium m-styrene-sulfonate, (d) sodium bromostyrenesulfonate and (e) sodium p-β-hydroxyethylbenzenesulfonate, respectively.

In FIG. 8, the ordinate shows the peak intensity (the absorption intensity of a detector, the unit is arbitrary), and the abscissa shows the elution time (the unit is minutes).

MODE FOR CARRYING OUT THE INVENTION

Figure 1:
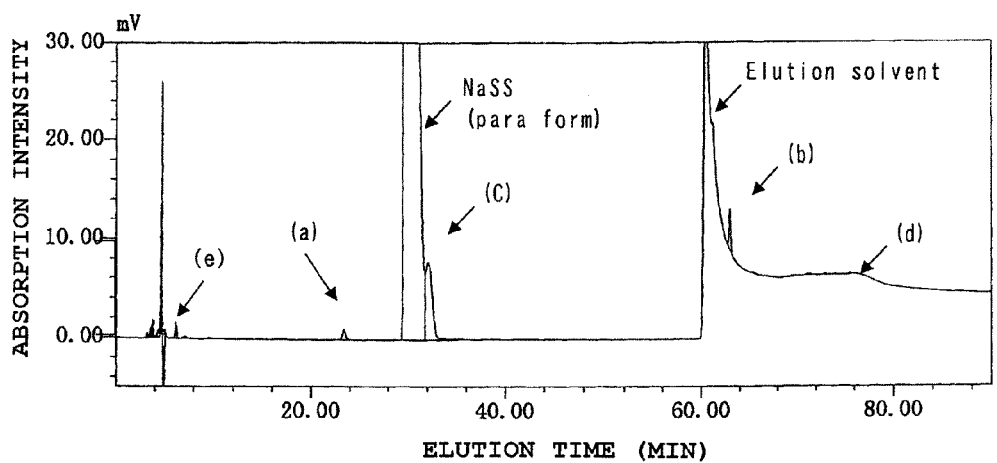
FIG. 1 shows HPLC chromatogram of high-purity sodium p-styrenesulfonate of Example 1.

The present invention relates to high-purity sodium p-styrenesulfonate with an excellent hue in which the iron content in sodium p-styrenesulfonate is less than 3.00 μg/g, the sodium bromide content is less than 2.50 wt %, and the peak area ratios of (a) sodium o-styrenesulfonate, (b) sodium p-β-bromoethylbenzenesulfonate, (c) sodium m-styrenesulfonate, (d) sodium bromostyrenesulfonate and (e) sodium p-β-hydroxyethylbenzenesulfonate, which are determined by high-performance liquid chromatography (HPLC), are (a) ≤0.40%, (b) ≤4.00%, (c) ≤8.00%, (d) ≤0.10% and (e) ≤0.80%, respectively (provided that the sum of peak areas of sodium p-styrenesulfonate and (a) to (e) is 100), and sodium PSS with an excellent hue having the above-mentioned repeating structural unit A or the above-mentioned repeating structural units A and B, which is produced using the same.

The term "with an excellent hue" used herein means not colored and nearly white or colorless and transparent. However, in the present invention, it particularly means low in yellowness. Specifically, in the case of high-purity sodium p-styrenesulfonate, it means that the yellowness (YI value) of a crystal powder determined with a color-difference meter is small, that the whiteness (WI value) is high, and that the APHA value of an aqueous solution is small. Further, in the case of sodium PSS, it means that the APHA value, the yellowness (YI value) and the b value of an aqueous solution of sodium PSS, which are determined with a color-difference meter, are small.

In the present invention, preferred are high-purity sodium p-styrenesulfonate in which the iron content in sodium p-styrenesulfonate is less than 3.00 μg/g, the sodium bromide content is less than 2.50 wt %, and the peak area ratios of (a) sodium o-styrenesulfonate, (b) sodium p-β-bromoethylbenzenesulfonate, (c) sodium m-styrene-sulfonate, (d) sodium bromostyrenesulfonate and (e) sodium p-β-hydroxyethylbenzenesulfonate, which are determined by HPLC, are (a) ≤0.20%, (b) ≤0.50%, (c) ≤3.00%, (d) ≤0.10% and (e) ≤0.20%, respectively (provided that the sum of peak areas of sodium p-styrenesulfonate and (a) to (e) is 100), and sodium PSS having the above-mentioned repeating structural unit A or the above-mentioned repeating structural units A and B, which is produced using the same.

Sodium PSS of the present invention is not limited to a homopolymer of sodium p-styrenesulfonate. That is to say, it is not particularly limited as long as it has the above-mentioned repeating structural unit A or the above-mentioned repeating structural units A and B, and may be a random copolymer, a block copolymer or a graft copolymer. The block copolymer as said herein is one in which a sodium PSS chain (the above-mentioned repeating structural unit A) and a polymer chain (the above-mentioned repeating structural unit B) different from sodium PSS are linked with each other in block form by a covalent bond, and includes a type such as a di-block, tri-block or multi-block type. Further, the graft copolymer is one in which branches of polymer chains (the above-mentioned repeating structural unit B) different from sodium PSS are bonded to a stem of sodium PSS (the above-mentioned repeating structural unit A), or branches of sodium PSS (the above-mentioned repeating structural unit A) are bonded to a stem of a polymer chain (the above-mentioned repeating structural unit B) different from sodium PSS, by covalent bonds in branch (graft) form.

The present invention is characterized in that the monomer (sodium p-styrenesulfonate) used for the production of sodium PPS is highly purified, and will be described below.

Commercially available sodium p-styrenesulfonate usually contains 5.0 to 10.0 wt % of water (crystallization water and adhesive water). This water is the greatest impurity contained in sodium p-styrenesulfonate. The points of the present invention are that in addition to sodium bromide (the case of M=sodium in the following formula) as a main impurity next to water, unreacted brominated intermediates, organic isomers and iron have been found to be contained as impurities, as can be seen from the following general production process of a p-styrenesulfonic acid salt, and that the hue of sodium p-styrenesulfonate has been found to be significantly improved by reducing these impurities.

[Chemical Formula 2]

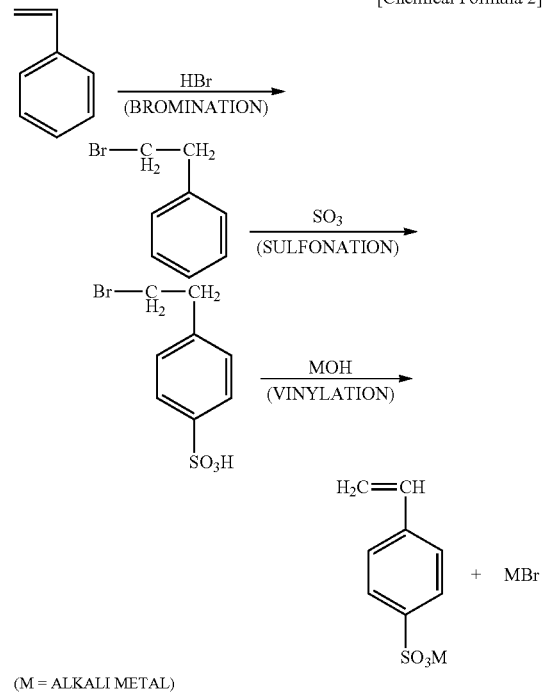

(M = ALKALI METAL)

As a result of detailed analysis of the impurities other than water, which are contained in sodium p-styrenesulfonate, it has become clear that small amounts of iron, (a) sodium o-styrenesulfonate, (b) sodium p-β-bromoethylbenzenesulfonate, (c) sodium m-styrene-sulfonate, (d) sodium bromostyrenesulfonate and (e) sodium p-β-hydroxyethylbenzenesulfonate are contained, in addition to sodium bromide as the main impurity.

The present inventors have produced high-purity sodium p-styrenesulfonate in which the iron content is less than 3.00 μg/g, the sodium bromide content is less than 2.50 wt %, and the peak area ratios of (a) sodium o-styrenesulfonate, (b) sodium p-β-bromoethylbenzenesulfonate, (c) sodium m-styrene-sulfonate, (d) sodium bromostyrenesulfonate and (e) sodium p-β-hydroxyethylbenzenesulfonate, which are determined by high-performance liquid chromatography (HPLC), are (a) ≤0.40%, (b) ≤4.00%, (c) ≤8.00%, (d) ≤0.10% and (e) ≤0.80%, respectively (provided that the sum of peak areas of sodium p-styrenesulfonate and (a) to (e) is 100), by a method of partially dissolving sodium p-styrenesulfonate containing the above-mentioned impurities in an aqueous solvent, followed by recrystallization, a method of washing with pure water, or controlling production conditions such as the reaction temperature. As a result, it has been found that the hue of sodium p-styrenesulfonate is significantly improved. Further, the above-mentioned impurities have been reduced to (a) ≤0.20%, (b) ≤0.50%, (c) ≤3.00%, (d) ≤0.10% and (e) ≤0.20%, respectively (provided that the sum of peak areas of sodium p-styrenesulfonate and (a) to (e) is 100). As a result, it has been found that the hue of sodium p-styrenesulfonate is further improved.

Furthermore, high-purity sodium PSS has been produced using the same by a conventional radical polymerization process. As a result, it has been found that the hue of sodium PSS is significantly improved. The high-purity sodium p-styrenesulfonate and sodium PSS have extremely excellent hues, so that the availability thereof in the above-mentioned industrial fields is extremely high. For example, (chloroprene rubber emulsion and) chloroprene rubber has been produced using the sodium PSS as a dispersant. As a result, it has been found that the hue of the chloroprene rubber is further improved, as compared to the case where conventional sodium PSS is used. Further, the sodium PSS has been used as synthetic starch for a clothing ironing agent. As a result, it has been found that the hue of cloth treated with the sodium p-styrenesulfonate is further improved, as compared to the case of cloth treated with conventional sodium PSS.

Although the reason why the hue of sodium p-styrenesulfonate has been improved is not necessarily clear, it is considered to be a synergistic effect due to reduction of iron and other impurities. The reason why the hue of sodium PSS has been improved is considered to be that the chemical stability of sodium PSS has been improved by reduction of isomers such as the meta form and the nuclear brominated form, and sodium p-β-haloethylbenzenesulfonate, in addition to these.

Although there is no limitation on the weight average molecular weight of sodium PSS of the present invention, which is determined by GPC, it is preferably from 2,000 to 1,000,000. In the case where used as a dispersant in emulsion polymerization, a relatively low molecular weight is preferred, in view of emulsion viscosity, stability and the like. For example, it is preferably from 2,000 to 50,000. On the other hand, in the case where used for purposes other than emulsion polymerization, for example, as synthetic starch for clothing finishing, a high molecular weight body is better in terms of viscosity and water resistance after drying, and it is preferably from 50,000 to 600,000 in view of handling properties.

This weight average molecular weight can be easily adjusted by the amount of a polymerization initiator or a chain transfer agent added to a monomer.

There is no particular limitation on another monomer other than sodium p-styrenesulfonate, which is used in sodium PSS of the present invention, as long as radical polymerization thereof proceeds through sodium PSS radicals, or as long as it produces radicals that can act as a radical polymerization initiator to sodium p-styrenesulfonate (in other words, it is radically polymerizable with sodium p-styrenesulfonate). Examples thereof include styrenes such as styrene, chlorostyrene, dichlorostyrene, bromostyrene, dibromostyrene, fluorostyrene, trifluorostyrene, nitrostyrene, cyanostyrene, α-methylstyrene, p-chloromethylstyrene, p-cyanostyrene, p-amino styrene, p-acetoxystyrene, p-styrenesulfonyl chloride, ethyl p-styrenesulfonyl, methyl p-styrenesulfonyl, propyl p-styrenesulfonyl, p-butoxystyrene, p-hydroxystyrene, 4-vinylbenzoic acid, 3-isopropenyl-α,α'-dimethylbenzyl isocyanate and vinylbenzyltrimethylammonium chloride, vinyl ethers such as isobutyl vinyl ether, ethyl vinyl ether, 2-phenyl vinyl alkyl ether, nitrophenyl vinyl ether, cyanophenyl vinyl ether, chlorophenyl vinyl ether and chloroethyl vinyl ether, acrylic acid esters such as methyl acrylate, ethyl acrylate, propyl acrylate, butyl acrylate, pentyl acrylate, hexyl acrylate, decyl acrylate, lauryl acrylate, octyl acrylate, dodecyl acrylate, stearylacrylate, 2-ethylhexylacrylate, cyclohexyl acrylate, bornyl acrylate, 2-ethoxyethyl acrylate, 2-butoxyethyl acrylate, 2-hydroxyethyl acrylate, tetrahydrofurfuryl acrylate, methoxyethylene glycol acrylate, ethylcarbitol acrylate, 2-hydroxypropyl acrylate, 4-hydroxybutyl acrylate, 3-(trimethoxysilyl)propyl acrylate, polyethylene glycol acrylate, glycidyl acrylate, 2-(acryloyloxy)ethyl phosphate, 2,2,3,3-tetrafluoropropyl acrylate, 2,2,2-trifluoroethyl acrylate, 2,2,3,3,3-pentafluoropropyl acrylate and 2,2,3,4,4,4-hexafluorobutyl acrylate, methacrylic acid esters such as methyl methacrylate, t-butyl methacrylate, sec-butyl methacrylate, i-butyl methacrylate, i-propyl methacrylate, decyl methacrylate, lauryl methacrylate, octyl methacrylate, dodecyl methacrylate, stearyl methacrylate, cyclohexyl methacrylate, bornyl methacrylate, benzyl methacrylate, phenyl methacrylate, glycidyl methacrylate, polyethylene glycol methacrylate, 2-hydroxyethyl methacrylate, tetrahydrofurfuryl methacrylate, methoxyethylene glycol methacrylate, ethylcarbitol methacrylate, 2-hydroxypropyl methacrylate, 4-hydroxybutyl methacrylate, 2-(methacryloyloxy)ethyl phosphate, 2-(dimethylamino)ethyl methacrylate, 2-(diethylamino)ethyl methacrylate, 3-(dimethylamino)propyl methacrylate, 2-(isocyanato)ethyl methacrylate, 2,4,6-tribromophenyl methacrylate, 2,2,3,3-tetrafluoropropyl methacrylate, 2,2,2-trifluoroethyl methacrylate, 2,2,3,3,3-pentafluoropropyl methacrylate, 2,2,3,4,4,4-hexafluorobutyl methacrylate and diacetone methacrylate, 1,3-butadienes such as isoprenesulfonic acid, 1,3-butadiene, 2-methyl-1,3-butadiene, 2-chloro-1,3-butadiene, 2,3-dichloro-1,3-butadiene, 2-cyano-1,3-butadiene, 1-chloro-1,3-butadiene, 2-(N-piperidylmethyl)-1,3-butadiene, 2-triethoxymethyl-1,3-butadiene, 2-(N,N-dimethylamino)-1,3-butadiene, N-(2-methylene-3-butenoyl)morpholine and diethyl 2-methylene-3-butenylphosphonate, maleimides such as N-phenylmaleimide, N-(chlorophenyl)maleimide, N-(methylphenyl)maleimide, N-(isopropylphenyl)maleimide, N-(sulfophenyl)maleimide, N-methylphenylmaleimide, N-bromophenylmaleimide, N-naphthylmaleimide, N-hydroxyphenylmaleimide, N-methoxyphenylmaleimide, N-carboxyphenylmaleimide, N-(nitrophenyl)maleimide, N-benzylmaleimide, N-(4-acetoxy-1-naphthyl)maleimide, N-(4-oxy-1-naphthyl)maleimide, N-(3-fluoranthyl)maleimide, N-(5-fluoresceinyl)maleimide, N-(1-pyrenyl)maleimide, N-(2,3-xylyl)maleimide, N-(2,4-xylyl)maleimide, N-(2,6-xylyl)maleimide, N-(aminophenyl)maleimide, N-(tribromophenyl)maleimide, N-[4-(2-benzimidazolyl)phenyl]maleimide, N-(3,5-dinitrophenyl)maleimide, N-(9-acridinyl)maleimide, maleimide, N-(sulfo-phenyl)maleimide, N-cyclohexylmaleimide, N-methylmaleimide, N-ethylmaleimide and N-methoxyphenylmaleimide, fumaric acid diesters such as dibutyl fumarate, dipropyl fumarate, diethyl fumarate and dicyclohexyl fumarate, fumaric acid monoesters such as butyl fumarate, propyl fumarate and ethyl fumarate, maleic acid diesters such as dibutyl maleate, dipropyl maleate and diethyl maleate, maleic acid monoesters such as butyl maleate, propyl maleate, ethyl maleate and cyclohexyl maleate, acid anhydrides such as maleic anhydride and citraconic anhydride, acrylamides such as acrylamide, N-methylacrylamide, N-ethylacrylamide, 2-hydroxyethyl-acrylamide, N,N-diethylacrylamide, acryloylmorpholine, N,N-dimethylaminopropylacrylamide, isopropylacrylamide, N-methylolacrylamide, sulfophenylacrylamide, 2-acrylamido-2-methylpropanesulfonic acid, 2-acrylamido-1-methylsulfonic acid, diacetoneacrylamide and acrylamidoalkyltrialkylammonium chloride, methacrylamides such as methacrylamide, N-methylmethacrylamide, N-ethylmethacrylamide, 2-hydroxyethylmeth-acrylamide, N,N-diethylmethacrylamide, N,N-di-methylmethacrylamide, N-methylolmethacrylamide, methacryloylmorpholine, N,N-dimethylaminopropylmethacrylamide, iso-propylmethacrylamide, 2-methacrylamido-2-methylpropanesulfonic acid and methacrylamidoalkyltrialkylammonium chloride, and in addition, vinylpyrrolidone, sulfophenylitaconimide, acrylonitrile, methacrylonitrile, fumaronitrile, α-cyanoethyl acrylate, citraconic acid, citraconic anhydride, vinyl acetate, vinyl propionate, vinyl pivalate, vinyl versatate, crotonic acid, itaconic acid, fumaric acid, maleic acid, mono-2-(methacryloyloxy)ethyl phthalate, mono-2-(methacryloyloxy)ethyl succinate, mono-2-(acryloyloxy)ethyl succinate, methacryloxypropyltri-methoxysilane, methacryloxypropyldimethoxysilane, acrolein, vinyl methyl ketone, N-vinylacetamide, N-vinylformamide, vinyl ethyl ketone, vinylsulfonic acid, allylsulfonic acid, dehydroalanine, sulfur dioxide, isobutene, N-vinylcarbazole, vinylidene dicyanide, p-quinodimethane, chlorotrifluoroethylene, tetrafluoroethylene, norbornene, N-vinylcarbazole, acrylic acid, methacrylic acid and the like. Among these, in view of copolymerizability with p-styrenesulfonic acid (salt), availability and the like, preferred are methacrylic acid (salt), methyl methacrylate, 2-hydroxyethyl methacrylate, glycidyl methacrylate, maleic anhydride, maleic acid (salt), N-phenylmaleimide, N-cyclohexylmaleimide, methacrylamide, methacryloylmorpholine, styrene and styrene derivatives.

The use ratio of the above-mentioned other monomer is 99 wt % or less and preferably about 10 to 90 wt %, in the total monomers. In the case of exceeding 99 wt %, the features of sodium p-styrenesulfonate can be imparted to the polymer by copolymerization of a tiny amount of sodium p-styrenesulfonate depending on the intended use. However, when used in the clothing finishing agent or the dispersant as the main use of the present invention, the characteristics of sodium p-styrenesulfonate becomes difficult to be exerted. This is therefore unfavorable.

The production method of high-purity sodium p-styrenesulfonate of the present invention is described below.

(1) As a method for removing iron that is the most important trace impurity in the present invention, there are (i) a method of removing iron ions by treating p-β-bromoethylbenzenesulfonic acid as a precursor of p-styrenesulfonic acid with a strong acid cation exchange resin, (ii) a method of filtering off water-soluble ferrous hydroxide from sodium p-styrenesulfonate obtained by a reaction of p-β-bromoethylbenzenesulfonic acid with sodium hydroxide and crystallization, (iii) a method of precipitating water-insoluble ferric hydroxide by blowing air into an aqueous alkali solution of sodium p-styrenesulfonate or adding a oxidizing agent thereto, and filtering off it, and the like.

In the case of the purification method of (i), more specifically showing the method for removing iron, for example, a sulfonic acid type cation exchange resin regenerated with hydrochloric acid is placed in an aqueous p-β-bromoethylbenzenesulfonic acid solution (70 to 80% of ion exchange capacity of the cation exchange resin), and slowly stirred at room temperature for 3 to 6 hours, followed by filtering off of p-β-bromoethylbenzenesulfonic acid, thereby being able to remove the iron ions.

Incidentally, using high-purity p-β-bromoethylbenzenesulfonic acid obtained, and then, according to the above-mentioned chemical reaction formula, vinylation may be performed by an ordinary method to obtain sodium p-styrenesulfonate. That is to say, as conditions of vinylation in this case, for example, there is a method of performing vinylation at 60 to 110° C. while concurrently feeding p-β-bromoethylbenzenesulfonic acid and sodium hydroxide in an amount of 2.0- to 3.0-fold moles, for example, 2-fold moles, based on that of p-β-bromoethyl-benzenesulfonic acid, to a stainless steel reaction tank provided with a jacket and equipped with a stirrer, over 2 to 5 hours.

Further, showing a specific example of the purification method of (ii), there is a method of removing impurities such as iron and sodium bromide from sodium p-styrenesulfonate crystals by subjecting a slurry containing crystals of sodium p-styrenesulfonate and water-soluble impurities such as ferrous hydroxide and sodium bromide to solid-liquid separation by centrifugal filtration.

Furthermore, showing a specific example of the purification method of (iii), water-soluble ferrous hydroxide is precipitated as water-insoluble ferric hydroxide by blowing air into an aqueous alkali solution of sodium p-styrenesulfonate, and thereafter, sodium p-styrenesulfonate crystals having a high specific gravity are sedimented and colloidal ferric hydroxide is suspended, by centrifugation. Suspended ferric hydroxide and impurities such as sodium bromide dissolved in water can be removed by decantation.

(2) Although a method for removing impurities other than iron is not particularly limited, the main impurities such as sodium bromide, the isomers and sodium p-β-haloethylbenzenesulfonate can be reduced, for example, by putting commercially available sodium p-styrene-sulfonate into pure water or a mixed solvent of a water-soluble solvent such as acetone, methanol, ethanol, isopropanol or acetonitrile and water, followed by heating, stirring and partial dissolution at 40 to 70° C. for 30 minutes to 1 hour, thereafter, performing cooling to 30° C. or less over 30 minutes to 2 hours, and washing or recrystallizing sodium p-styrenesulfonate. The impurities other than iron can be reduced by repeating this operation. This recrystallization operation is performed at least once, and preferably 1 to 3 times in view of productivity and cost.

More specifically showing the above-mentioned purification method of (2), high-purity sodium p-styrene-sulfonate can be obtained, for example, by dissolving sodium p-styrenesulfonate in methanol by heating at a concentration of 5 to 6 wt % (usually, at 40 to 50° C. for about to 60 minutes), precipitating crystals of sodium p-styrenesulfonate by slow cooling to ordinary temperature to near 10° C., and performing drying and filtration.

High-purity sodium p-styrenesulfonate obtained by treatment according to the above purification method (1) may be further subjected to purification treatment according to the above-mentioned purification method (2). By this treatment, the amounts of the impurities such as iron and sodium bromide, particularly the amounts of (a) sodium o-styrenesulfonate, (b) sodium p-β-bromoethylbenzenesulfonate, (c) sodium m-styrene-sulfonate, (d) sodium bromostyrenesulfonate and (e) sodium p-β-hydroxyethylbenzenesulfonate, can be further reduced.

Another characteristic of the present invention is that the particle size, the water content and the like of sodium p-styrenesulfonate are specified within the specific ranges, and will be described below.

That is to say, sodium p-styrenesulfonate (the case where M in [Chemical Formula 2] described above is sodium) is generally produced by the process of [Chemical Formula 2] described above, and the shape and grain size thereof are considered to be mainly influenced by conditions of the vinylation process (reaction crystallization).

It has been found that in the case where sodium p-styrenesulfonate is used in large amounts as a chemical raw material, when the median diameter is as small as less than 25.00 µm, fluidity thereof is insufficient, although solubility in water is good, resulting in easy occurrence of clogging in a raw material charging hopper, whereas when the median diameter exceeds 150.00 µm, the rate of dissolution thereof is significantly decreased, although fluidity is improved, resulting in easy occurrence of clogging of a strainer.

Further, the present inventors have found that when the median diameter of sodium p-styrenesulfonate is less than 25.00 µm, or when small particles less than 10.00 µm exceeds 10.00%, filterability (liquid drainability) is deteriorated to fail to efficiently perform purification, in the case where the sodium p-styrenesulfonate is washed or purified by recrystallization using an aqueous solvent.

Thus, the present invention is sodium p-styrenesulfonate characterized in that it is composed of particles having a median diameter measured with a laser diffraction/scattering particle size analyzer of 25.00 to 150.00 µm and a content of small particles less than 10.00 µm of 10.00% or less, and has a water content of 10.00 wt % or less and a repose angle of 55 degrees or less. In terms of a balance between fluidity and solubility, more preferably, it is composed of particles having a median diameter of 40.00 to 90.00 µm and a content of small particles less than 10.00 µm of 3.00% or less, and has a water content of 8.00 wt % or less and a repose angle of 50 degrees or less.

As described above, when the median diameter of sodium p-styrenesulfonate is less than 25.00 µm, or when small particles less than 10.00 µm exceeds 10.00%, filterability (liquid drainability) is deteriorated to fail to efficiently perform purification, in the case where the sodium p-styrenesulfonate is washed or purified by recrystallization using an aqueous solvent. On the other hand, when it exceeds 150.0 µm (as a result of decreased water content), fluidity is good, and filterability in the case where washed or purified by recrystallization is also good. However, solubility is deteriorated.

Here, in order to adjust the above-mentioned median diameter to the range of 25.00 to 150.00 µm, preferably to the range of 40.00 to 90.00 µm, the rate of crystallization may be controlled by adjusting the above-mentioned reaction crystallization conditions, that is to say, the feed conditions of p-β-bromoethylbenzenesulfonic acid and sodium hydroxide as raw materials and the reaction temperature.

Further, in order to adjust the small particles less than 10.00 µm to 10.00% or less, preferably to 3.00% or less, the median diameter may be adjusted so as to become 25.00 µm or more by the above-mentioned method, whereby the small particles less than 10.00 µm are necessarily decreased.

Figure 5:
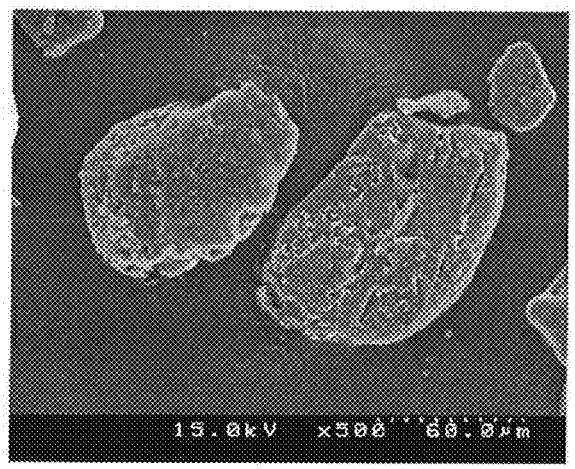
FIG. 5 shows a scanning electron microscope image (magnification: ×500) of sodium p-styrenesulfonate of Example 6.

Sodium p-styrenesulfonate of the present invention is composed of the particles having a median diameter within the above-mentioned specific range, which are preferably "elliptic disk-shaped secondary particles." The "elliptic disk-shaped secondary particles" as used herein are elliptic disk-shaped particles as shown in an electron micrograph of FIG. 5, and are aggregates of many crystals (primary particles) of sodium p-styrenesulfonate hemihydrate formed by physical force. In sodium p-styrenesulfonate of the present invention, the reason why the particles obtained become the "elliptic disk-shaped secondary particles" is not clear. However, the reason for this is considered to be that aggregation occurs by the action of physical force such as the rate of crystallization during reaction crystallization, stirring conditions and forced fluidization described later.

Sodium p-styrenesulfonate is preferably a hemihydrate because of its excellent storage stability, and water (crystallization water) in sodium p-styrenesulfonate hemihydrate is theoretically 4.18 wt %. Accordingly, water exceeding 4.18 wt % is adhesive water. The smaller the median diameter of sodium p-styrenesulfonate is, the more the adhesive water increases by an increase in the total surface area. As a result, fluidity is reduced. On the other hand, the larger the median diameter is, the more the adhesive water decreases by a decrease in the total surface area. As a result, fluidity is considered to have been improved. An increase in the adhesive water means not only a reduction in fluidity but also a decrease in purity (the sodium p-styrenesulfonate content per product wet weight) of sodium p-styrenesulfonate. This is therefore practically unfavorable.

From this point, sodium p-styrenesulfonate of the present invention is a hemihydrate having a water content of 10.00% by weight or less, preferably 8.0% by weight or less, and more preferably 4.5 to 7.0% by weight. When the water content exceeds 10% by weight, fluidity is reduced, regardless of the particle size of sodium p-styrenesulfonate. Further, it means a decrease in purity of wet products. This is therefore unfavorable. In order to obtain sodium p-styrenesulfonate of the present invention as the hemihydrate having a water content of 10% or less, as described above, the median diameter may be adjusted to 25.00 µm or more by adjusting the above-mentioned reaction crystallization conditions, that is to say, the feed conditions of p-β-bromoethylbenzenesulfonic acid and sodium hydroxide as the raw materials and the reaction temperature, thereby controlling the rate of crystallization.

Further, in sodium p-styrenesulfonate of the present invention, the repose angle defined later is 55 degrees or less, and preferably 50 degrees or less. When it exceeds 55 degrees, fluidity is deteriorated. When the repose angle is 55 degrees or less, fluidity is excellent, and a trouble such as clogging in a hopper at the time when used in large amounts in a factory is solved. This is therefore preferred. In order to decrease the repose angle, fluidity of a powder may be increased. The relationship between the fluidity and the structure and composition of the sodium p-styrenesulfonate powder is not necessarily clear. However, the influence of water in the powder is considered to be significant. That is to say, the smaller the particle size of the powder is, the more the water content is increased by an increase in the total surface area. As a result, fluidity is considered to be reduced, and the water content can be adjusted by the above-mentioned particle size control.

Incidentally, solubility of sodium p-styrenesulfonate of the present invention in water (see "measurement of the rate of dissolution" described later) is preferably 200 seconds or less, and more preferably 160 seconds or less. There is no adverse effect due to excessively high solubility. However, when it exceeds 200 seconds, troubles such as a decrease in productivity and clogging of a strainer are liable to occur at the time when used in large amounts in a factory. This is therefore unfavorable. This solubility can be adjusted by the above-mentioned particle size control.

The production method of sodium p-styrenesulfonate of the present invention will be described below. Although the production method of sodium p-styrenesulfonate is not particularly limited, it is important to perform reaction crystallization at 60 to 110° C. for 1 to 7 hours, for example, while feeding so as to keep the concentration of sodium hydroxide in a reaction tank [(the weight of total sodium hydroxide fed/the weight of the total reaction solution in the reaction tank)×100] at 10.00 to 20.00 wt % and so as to increase the p-β-bromoethylbenzenesulfonic acid concentration [(the weight of total p-β-bromoethylbenzenesulfonic acid fed/the weight of the total reaction solution in the reaction tank)×100] from 0.00 wt % to 30.00 to 50.00 wt % over 1 to 7 hours. A slurry of sodium p-styrenesulfonate produced is preferably cooled to 10 to 40° C., and thereafter, subjected to solid-liquid separation, for example, using a centrifugal filter to obtain a wet cake of sodium p-styrenesulfonate. Then, the wet cake is forcedly fluidized using a single-screw type blender, for example, at 20 to 40° C. for 5 to 30 minutes, thereby being able to produce a hemihydrate of sodium p-styrenesulfonate of the present invention.

For example, when p-β-bromoethylbenzenesulfonic acid is fed so as to have a concentration of 70 wt % to an aqueous sodium hydroxide solution having a concentration exceeding 20 wt % in the whole reaction solution (for example, Japanese Patent No. 3601222), sodium p-styrenesulfonate crystals obtained become too small, so that sodium p-styrenesulfonate hemihydrate having a high water content and inferior in fluidity is obtained. Further, when washing or recrystallization purification is performed using an aqueous solvent, solid-liquid separability is deteriorated to degrade the purification efficiency. On the other hand, even when the concentration of sodium hydroxide in the whole reaction solution is 20 wt % or less, in the case where the feed rate of p-β-bromoethylbenzenesulfonic acid is too high (Japanese Patent No. 3890642), for example, in the case where the concentration of p-β-bromoethylbenzenesulfonic acid in the whole reaction solution exceeds 40 wt % within one hour after the start of feed, the sodium p-styrenesulfonate crystals obtained become too large. Accordingly, sodium p-styrenesulfonate hemihydrate that is good in fluidity but inferior in solubility is obtained.

Sodium p-styrenesulfonate produced in the present invention is controlled in particle size by improvement of the reaction crystallization conditions, and improved in fluidity while keeping excellent solubility, so that handling properties thereof is good. Further, high-purity sodium p-styrenesulfonate can be efficiently produced. It is therefore useful in the above-mentioned industrial fields.

The production method of sodium PSS of the present invention will be described below.

Although the production method of sodium PSS is not particularly limited, a method according to ordinary radical polymerization is exemplified as a first example. For example, a reaction container is charged with a homogeneous solution of a mixture of water or an aqueous solvent, sodium p-styrenesulfonate and another monomer radically copolymerizable with sodium p-styrenesulfonate as needed, and a molecular weight regulator is added thereto as needed. The inside of the system is deoxidized, followed by heating to a specific temperature, and polymerization may be conducted while adding a radical polymerization initiator. In this case, in order to avoid rapid polymerization and in the case of considering molecular weight controllability in a low molecular weight region, it is preferred that the respective monomers are continuously added little by little to the reaction container, together with the polymerization initiator and molecular weight regulator, without charging the reaction container with the whole monomer mixture at first. Further, sodium PSS can also be produced by finely dispersing or emulsifying an aqueous solution of a water-soluble monomer such as sodium p-styrenesulfonate in oil, and thereafter performing polymerization while adding a radical polymerization initiator (so-called inverse emulsion polymerization).

The reaction solvent is not particularly limited. However, in view of solubility of sodium p-styrenesulfonate and the other copolymerizable monomer (comonomer), and use as the dispersant in emulsion polymerization and use as the synthetic starch in the clothing finishing agent, a mixture of water and an aqueous solvent is preferred. There is no limitation on the aqueous solvent as long as it dissolves a mixture of sodium p-styrenesulfonate and the comonomer. Examples thereof include acetone, tetrahydrofuran, dioxane, methanol, ethanol, n-propanol, isopropanol, methoxyethanol, 2-ethoxyethanol, 2-butoxyethanol, butanol, ethylene glycol, 1-methoxy-2-propanol, propylene glycol-1-monomethylether-2-acetate, propylene glycol, glycerol, dimethyl sulfoxide, dimethylformamide, N-methylpyrrolidone and the like. Preferred are acetone, ethanol, isopropanol, tetrahydrofuran, dioxane, dimethyl sulfoxide, N-methylpyrrolidone and dimethylformamide.

The amount used of water or the aqueous solvent as a reaction solvent is usually from 150 to 2,000 parts by weight based on 100 parts by weight of the total amount of the monomers.

Although the molecular weight regulator is not particularly limited, examples thereof include disulfides such as diisopropylxanthogen disulfide, diethylxanthogen disulfide, diethylthiuram disulfide, 2,2'-dithiodipropionic acid, 3,3'-dithiodipropionic acid, 4,4'-dithiobutanoic acid and 2,2'-dithiobis(benzoic acid), mercaptans such as n-dodecyl mercaptan, octyl mercaptan, t-butyl mercaptan, thioglycolic acid, thioacetic acid, thiomalic acid, 2-mercaptopropionic acid, 3-mercaptopropionic acid, thiosalicylic acid, 3-mercaptobenzoic acid, 4-mercaptobenzoic acid, thiomalonic acid, dithiosuccinic acid, thiomaleic acid, thiomalic anhydride, dithiomaleic acid, thioglutaric acid, cysteine, homocysteine, 5-mercaptotetrazoleacetic acid, 3-mercapto-1-propanesulfonic acid, 3-mercaptopropane-1,2-diol, mercaptoethanol, 1,2-dimethylmercaptoethane, 2-mercaptoethylamine hydrochloride, 6-mercapto-1-hexanol, 2-mercapto-1-imidazole, 3-mercapto-1,2,4-triazole, N-acylcysteine, glutathione, N-butylaminoethanethiol, N,N-diethylaminoethanethiol, thiophenol and aminothiophenol, halogenated hydrocarbons such as iodoform, diphenylethylene, p-chlorodiphenylethylene, p-cyanodiphenylethylene, α-methylstyrene dimer, benzyl dithiobenzoate, 2-cyanoprop-2-yl dithiobenzoate, organic tellurium compounds, sulfur, sodium sulfite, potassium sulfite, sodium bisulfite, potassium bisulfite, sodium pyrosulfite, potassium pyrosulfite and the like.

The amount used of the molecular weight regulator is usually from 0.1 to 10 parts by weight based on 100 parts by weight of the total amount of the monomers.

The above-mentioned radical polymerization initiators include, for example, peroxides such as di-t-butyl peroxide, dicumyl peroxide, t-butylcumyl peroxide, benzoyl peroxide, dilauryl peroxide, cumene hydroperoxide, t-butyl hydroperoxide, 1,1-bis(t-butylperoxy)-3,5,5-trimethylcyclohexane, 1,1-bis(t-butylperoxy)cyclohexane, cyclohexanone peroxide, t-butyl peroxybenzoate, t-butyl peroxyisobutyrate, t-butyl peroxy-3,5,5-trimethylhexanoate, t-butyl peroxy-2-ethylhexanoate, t-butyl peroxyisopropylcarbonate, cumyl peroxyoctoate, potassium persulfate, ammonium persulfate and hydrogen peroxide, azo compounds such as 2,2'-azobis(4-methoxy-2,4-dimethylvaleronitrile), 2,2'-azobis(2,4-dimethylvaleronitrile), 2,2'-azobis(2-methylpropionitrile), 2,2'- azobis(2-methylbutyronitrile), 1,1'-azobis(cyclohexane-1-carbonitrile), 1-[(1-cyano-1-methylethyl)azo]-formamide, dimethyl 2,2'-azobis(2-methylpropionate), 4,4'-azobis(4-cyanovaleric acid), 2,2'-azobis(2,4,4-trimethylpentane), 2,2'-azobis{2-methyl-N-[1,1'-bis(hydroxy-methyl)-2-hydroxyethyl]propionamide}, 2,2'-azobis(2-(2-imidazolin-2-yl)propane]dihydrochloride, 2,2'-azobis(2-(2-imidazolin-2-yl)propane]disulfate dihydrate, 2,2'-azobis{2-[1-(2-hydroxyethyl)-2-imidazolin-2-yl)propane]}dihydrochloride, 2,2'-azobis(1-imino-1-pyrrolidino-2-methylpropane)dihydrochloride, 2,2'-azobis(2-methylpropionamidine)dihydrochloride and 2,2'-azobis[N-(2-carboxy-ethyl)-2-methylpropionamidine]tetrahydrate, and the like. Further, a reducing agent such as ascorbic acid, erythorbic acid, aniline, a tertiary amine, Rongalite, hydrosulfite, sodium sulfite or sodium thiosulfate may be used in combination, as needed.

The amount used of the radical polymerization initiator is usually from 0.1 to 10 parts by weight based on 100 parts by weight of the total amount of the monomers.

Although the polymerization conditions are not particularly limited, heating may be performed at 20 to 120° C. for 4 to 50 hours, under an inert gas atmosphere, and the conditions may be appropriately adjusted depending on the polymerization solvent, the monomer composition and the kind of polymerization initiator.

Sodium PSS of the present invention can also be produced by the above-mentioned general radical polymerization. However, when a living polymerization method is applied, it is also possible to narrow a molecular weight distribution or to produce a block copolymer.

To a polar monomer such as sodium p-styrenesulfonate, a living radical polymerization method is more preferred.

The living radical polymerization methods include, for example, an atom transfer polymerization method, a stable nitroxyl mediating polymerization method, a reversible addition fragmentation transfer polymerization method, an organic tellurium mediating polymerization method (Kobunshi Ronbunshu, Vol. 64, No. 6, pp. 329, 2007), a iodine transfer polymerization method (JP-A-2007-92014; Kobunshi Ronbunshu, Vol. 59, No. 10, page 798, 2010; Catalyst, Vol. 54, No. 4, page 257, 2012), a polymerization method using a complex of phosphine and carbon disulfide (JP-A-2006-233012), a method using trialkylborane (Adhesion, Vol. 50, No. 4, page 23, 2006) and a method using α-methylstyrene dimer (JP-A-2000-169531), and these methods can be applied also to the present invention.

As a specific example of living radical polymerization, after living radical polymerization of a radically polymerizable monomer other than sodium p-styrenesulfonate in an aqueous solvent, sodium p-styrenesulfonate of the present invention is added thereto, followed by further continuing the living polymerization, or after living radical polymerization of sodium p-styrenesulfonate in an aqueous solvent, another radically polymerizable monomer is added thereto, followed by further continuing the living radical polymerization. For example, a PSS block copolymer can be produced by performing such living radical polymerization.

Sodium PSS of the present invention may be randomly copolymerized with a monomer radically copolymerizable with sodium p-styrenesulfonate, as needed. Although there is no particular limitation, such monomers include, for example, the monomers described in the description of the sodium PSS block copolymer.

A production method of chloroprene will be described below. This production method is not particularly limited, and a known method can be applied (for example, see Japanese Patent No. 3601136 described above).

For example, a reaction container equipped with a stirrer and a jacket for temperature control is charged with water, a monomer such as chloroprene, an emulsifier, a dispersant, a molecular weight regulator and a pH adjuster as needed, and oxygen in the system is removed. After the monomer is sufficiently emulsified, polymerization may be performed at a predetermined temperature while adding a radical initiator. When desired to more increase crystallinity or cohesive force of chloroprene, the radical initiator and a reducing agent may be used in combination to perform polymerization at low temperature. The polymerization temperature is from 10 to 50° C., and polymerization is performed for 3 to 10 hours. At the time of reaching a desired polymerization conversion rate, a polymerization inhibitor is added to terminate the polymerization. As the molecular weight regulator, polymerization initiator and reducing agent, there can be used ones used in the production of sodium PSS. Further, in order to impart polarity and cohesive force to the chloroprene rubber obtained above, a hard component such as polymethyl methacrylate may be graft polymerized.

The above-mentioned emulsifier is not particularly limited. However, anionic emulsifiers include, for example, rosin acid salts, fatty acid salts, alkenyl succinates, alkyl ether carboxylates, alkyl diphenyl ether disulfonates, alkane sulfonates, alkyl succinate sulfonates, polyoxyethylene polycyclic phenyl ether sulfates, α-olefin sulfonates, alkylbenzene sulfonates, polyacrylic acid ester-acrylic acid copolymers, polymethacrylic acid ester-methacrylic acid copolymers, polyacrylamide-acrylic acid copolymers, polymethacrylamide-methacrylic acid copolymers, alkyl sulfosuccinates, alkyl sulfate ester salts, alkyl ether sulfate ester salts, sulfate ester salts of alkyl propenylphenol polyethylene oxide adducts, sulfate ester salts of allyl alkylphenol polyethylene oxide adducts, alkyl phosphate ester salts, polyoxyethylene alkyl ether phosphate ester salts, sulfates of higher fatty acid amides, sulfate ester salts of higher fatty acid alkylolamides and the like, nonionic emulsifiers include, for example, polyoxyalkylene alkyl amines, alkyl alkanol amides, amine oxide-based nonionic emulsifiers, polyoxyethylene alkyl ethers, polyoxyethylene alkyl phenyl ethers, polyoxyalkylene polycyclic phenyl ethers, alkyl propenyl phenol polyethylene oxide adducts, allyl alkyl phenol polyethylene oxide adducts, polyoxyethylene fatty acid esters, polyoxyethylene sorbitan fatty acid esters, sorbitan fatty acid esters, glycerin fatty acid esters, alkyl polyglucoxides, sucrose fatty acid esters, polyoxyethylene polyoxypropylene glycol, polyvinyl alcohol, carboxymethyl cellulose, polyvinylpyrrolidone, hydroxyethyl cellulose, polyacrylamide, polymethacrylamide, polydimethylaminoethyl methacrylate, polydimethylaminoethyl acrylate, polydiethylaminoethyl methacrylate, polydiethylaminoethyl acrylate, poly-t-butylaminoethyl methacrylate, poly-t-butylaminoethyl acrylate, polydimethylaminoethyl methacrylate/methyl methacrylate copolymers, polydimethylaminoethyl acrylate/methyl methacrylate copolymers, polydimethylaminoethyl methacrylate/butyl acrylate copolymers, polydimethylaminoethyl acrylate/ethyl acrylate copolymers and the like, cationic emulsifiers include, for example, alkyl amine salts, alkyl type quaternary ammonium salts, fatty acid amidoamine salts, alkyl amino acid salts and the like, and amphoteric emulsifiers include, for example, alkyldimethylaminoacetic acid betaines, alkyl dimethylamino sulfobetaines, alkyl sulfobetaines and the like.

The above-mentioned dispersants include, for example, naphthalene sulfonate salt formalin condensates, taurine derivatives, poly(p-styrenesulfonic acid) (salts), poly-(p-styrenesulfonic acid)/methacrylic acid copolymers (salts), poly(p-styrenesulfonic acid)/acrylic acid copolymers (salts), poly(p-styrenesulfonic acid)/acrylic acid ester copolymers (salts), p-styrenesulfonic acid/maleic acid copolymers (salts), p-styrenesulfonic acid/acrylamide copolymers (salts), p-styrenesulfonic acid/methacrylamide copolymers (salts), p-styrenesulfonic acid/2-hydroxyethyl methacrylate copolymers (salts), p-styrenesulfonic acid/vinylpyrrolidone copolymers (salts), poly(vinylphosphonic acid) copolymers (salts), poly(vinylsulfonic acid) copolymers (salts), poly(isoprenesulfonic acid) copolymers (salts) and the like, and particularly preferred is high-purity sodium PSS of the present invention.

High-purity sodium p-styrenesulfonate of the present invention has an extremely excellent hue, as compared to a conventional product, so that high-purity sodium p-styrenesulfonate and sodium PSS obtained by using the same act as an extremely useful reactive emulsifier and dispersant in the production of a polymer emulsion such as chloroprene rubber.

Sodium PSS with an excellent hue produced by the present invention not only can be utilized as the dispersant for producing the polymer emulsion such as the chloroprene rubber described above, but also is extremely useful as a dispersant for producing various aqueous dispersions such as synthetic starch for clothing ironing, personal care products, antistatic agents and pigments. In the case where used as the synthetic starch in the ironing agent for clothing, specific embodiments thereof include an example of incorporating a silicone polymer (acting as a smoothing agent), propylene glycol (acting as a stabilizing agent), a preservative, a fragrance ingredient and the like in the aqueous sodium PSS solution of the present invention.

EXAMPLES

The present invention is described in further detail with reference to the following examples. However, the present invention should not be construed as being limited by these examples in any way.

Incidentally, in the following examples, analysis and evaluation of p-β-haloethylbenzenesulfonic acid, sodium p-styrenesulfonate, sodium PSS and chloroprene rubber were performed under the following conditions.
<Quantitative Determination of Iron Content in p-β-Haloethylbenzenesulfonic Acid and Sodium p-Styrenesulfonate by IPC-MS>

In a 25-ml polyethylene measuring flask, about 0.1 g of a sample was accurately weighed, and 1 ml of 68% high-purity nitric acid was added thereto. After filling up to the gauge line, the iron content was quantitatively determined with an inductively-coupled plasma mass spectrometer, NexION 300S, manufactured by PerkinElmer, Inc.
<Measurement of Concentration of Aqueous p-β-Bromoethylbenzenesulfonic Acid Solution by HPLC>

A sample was dissolved in the following eluent A to prepare a solution having a concentration of 1.2 to 1.5 mg/ml, followed by performing HPLC analysis. Measurement conditions are as follows. Incidentally, a calibration curve was prepared using a 70 wt % aqueous p-β-bromoethylbenzenesulfonic acid solution as a standard.

Model=LC-8020 manufactured by Tosoh Corporation (degasser: SD-8022, pump: CCPM-II, column oven: CO-8020, ultraviolet-visible detector: UV-8020)

Column=TSKgel ODS-80TsQA (4.6 mm×25 cm)
Eluent=solution A) water/acetonitrile volume ratio=95/5+0.1 wt % trifluoroacetic acid
solution B) water/acetonitrile volume ratio=80/20+0.1 wt % trifluoroacetic acid
Gradient conditions=solution A 100% until 55 minutes, solution B 100% from 55 to 95 minutes
Flow rate=0.8 ml/min, UV detection conditions=230 nm, column temperature=ordinary temperature, injection amount=20 µl
<Quantitative Determination of Water Content in Sodium p-Styrenesulfonate>

In a weighing bottle (55 mm in diameter×30 mm in height), 2 g of a sample was weighed up to a digit of 0.1 mg, and dried with a drier (105±5° c.) for 90 minutes. After immediately transferred to a desiccator and cooled to room temperature, the mass thereof was measured up to a digit of 0.1 mg, and the water content was calculated from the following equation:

$$\text{Water content (wt \%)} = 100 \times [(a-b)/S]$$

a=weight (g) of the weighing bottle and the sample before drying, b=weight (g) of the weighing bottle and the sample after drying, S=sample amount (g)
<Quantitative Determination of Sodium p-Styrenesulfonate Content (Pure Content) in Sample>

Active double bonds were quantitatively determined by a redox titration method, and defined as the sodium p-styrenesulfonate content (that is to say, containing not only the para form but also the ortho and meta forms) in the sample.
(1) Instruments and Apparatus
1) Weighing bottle: 50 mm in diameter, 70 mm in depth
2) 500-ml and 1000-ml measuring flasks
3) 500-ml Erlenmeyer flask with stopper
4) Electronic chemical balance
(2) Reagents
1) Bromine solution: 22.00 g of potassium bromide (KBr) and 3.00 g of potassium bromate ($KBrO_3$) were dissolved in pure water to bring the total volume to 1,000 ml.
2) Aqueous sulfuric acid solution: (concentrated sulfuric acid/pure water volume ratio=1/1)
3) Aqueous potassium iodide solution: (200 g/liter)
4) 0.1 mol/liter aqueous sodium thiosulfate
5) Aqueous starch solution: 6.00 g of starch was dissolved in pure water to bring the total volume to 1,000 ml.
(3) Operations
1) In the weighing bottle, 20 g of a sample is weighed up to a digit of 0.1 mg.
2) The sample is washed and transferred with pure water to the 500-ml measuring flask to bring the liquid volume to about 400 ml.
3) A magnetic rotor is placed therein to perform stirring, thereby dissolving the sample.
4) The rotor is taken out, and adjustment to a marked line with pure water is performed, followed by shaking to prepare a test solution.
5) Into the 500-ml Erlenmeyer flask with stopper containing 200 ml of pure water, 25 ml of the bromine solution is added thereto.
6) After addition of 5 ml of the test solution, 10 ml of the aqueous sulfuric acid solution is added, and the flask is tightly stoppered, followed by standing for 20 minutes.
7) The aqueous potassium iodide solution (10 ml) is quickly added, followed by standing for 10 minutes.
8) Titration is performed with the aqueous sodium thiosulfate, and after the yellow color of the solution becomes pale, 1 ml of the starch solution is added as an indicator. The titration is performed until the blue color of iodine starch produced disappears.

9) Separately, as a blank test, 200 ml of pure water is added into the Erlenmeyer flask with stopper, and 25 ml of the bromine solution is added thereto. Then, 10 ml of the aqueous potassium iodide solution and 10 ml of aqueous sulfuric acid solution are quickly added, and the operation of 8) is performed.

(4) Calculation

The sodium p-styrenesulfonate content is calculated by the following equation:

$$A = 100 \times \{[0.01031 \times (a-b) \times f]/(S \times 5/500)\}$$

A: sodium p-styrenesulfonate content (%)
a: aqueous sodium thiosulfate solution (ml) required in the blank test
b: aqueous sodium thiosulfate solution (ml) required in the actual test
f: titer of the aqueous sodium thiosulfate solution
S: sample amount (g)

<Quantitative Determination of Sodium Bromide in Sodium p-Styrenesulfonate>

(1) Preparation of Sample

In a weighing bottle (50 mm in diameter×70 mm), 20 g of a sample was weighed up to a digit of 0.1 mg, and the sample was washed and transferred with pure water to a 500-ml measuring flask to bring the liquid volume to about 400 ml. A magnetic rotor was placed therein to perform stirring and dissolution. Thereafter, the rotor was taken out, and pure water was added thereto up to a marked line, followed by shaking. In a 100-ml measuring flask, 5 ml of the solution was correctly collected, and pure water was added thereto up to a marked line to prepare a sample solution.

The above-mentioned sample solution and a mixed standard solution (prepared so as to satisfy Br=5,000 μg/100 ml, Cl=500 μg/100 ml and SO₄=2,000 μg/100 ml, using standard solutions manufactured by Kanto Chemical Co., Inc.) were injected into an ion chromatograph, and the sodium bromide amount in the sample was calculated from each peak area.

(2) Measurement Conditions

Model=Ion Chromatography System 8020 manufactured by Tosoh Corporation
Column=TSK-Gel IC-Anion-PW
Column temperature=40° C.
Sample injection amount=100 μl
Flow rate=0.7 ml
Eluent=pure water was added to 5 g of potassium hydrogen phthalate and 300 ml of acetonitrile to bring a total amount of 3000 ml.

(3) Calculation

The content of sodium bromide (NaBr) was calculated by the following equation:

$$A = [[(5{,}000 \; \mu g \times 1.288 \times a/b) + (500 \; \mu g \times 2.899 \times c/d)]/(S \times 5/500)] \times 10^{-4}$$

A: content (%) of sodium bromide (NaBr)
a: sample area (Br)
b: standard area (Br)
c: sample area (Cl)
d: standard area (Cl)
S: sample amount (g)

<Analysis of Impurities in Sodium p-Styrenesulfonate by HPLC>

Measurement conditions are the same as in the case of the above-mentioned measurement of the concentration of the aqueous p-β-bromoethylbenzenesulfonic acid solution. A sodium p-styrenesulfonate sample (wet sample containing crystallization water and adhesive water) was dissolved in the above-mentioned eluent A to prepare a solution having a concentration of 0.5 mg/ml, which was subjected to HPLC analysis. The content rates of respective impurities (a) to (e) are area ratios, taking the sum of HPLC peak areas of sodium p-styrenesulfonate and (a) to (e) detected under the present conditions as 100.

Incidentally, each peak was previously identified by the following method.

Each component detected by HPLC was fractionated and treated with a cation exchange resin to convert a p-styrenesulfonate to a sulfonic acid type. Thereafter, a sulfonic acid group was methyl esterified by diazomethane, and gas chromatograph mass spectrometry (M-80B manufactured by Hitachi, Ltd.), Fourier transform infrared spectrometry (manufactured by PerkinElmer, Inc., System 2000), organic element analysis (manufactured by Yanaco, CHN Coder MT-3) and nuclear magnetic resonance analysis (manufactured by Varian Corporation, VXR-300) were performed to determine the structure thereof.

<Shape Observation>

Using a field-emission type scanning electron microscope (S-4500 manufactured by Hitachi, Ltd.), observation was performed at an accelerating voltage of 15 kV.

<Measurement of Particle Size Distribution>

In a 30-ml glass sample bottle, 0.55 g of a sample and 15.0 g of isopropanol were collected, and treated with an ultrasonic washer for 4 minutes while keeping the temperature at 25° C. or less to prepare a slurry. Thereafter, the particle size (median diameter) distribution was measured under the following conditions, using a laser diffraction/scattering type particle size analyzer, Microtrack HRA (manufactured by Nikkiso Co., Ltd.).

Particle transparency=Transp
Spherical particles=No
Particle refractive Index=1.55
Fluid refractive Index=1.38

<Measurement of Repose Angle>

(1) Instruments and Apparatus

Figure 3:
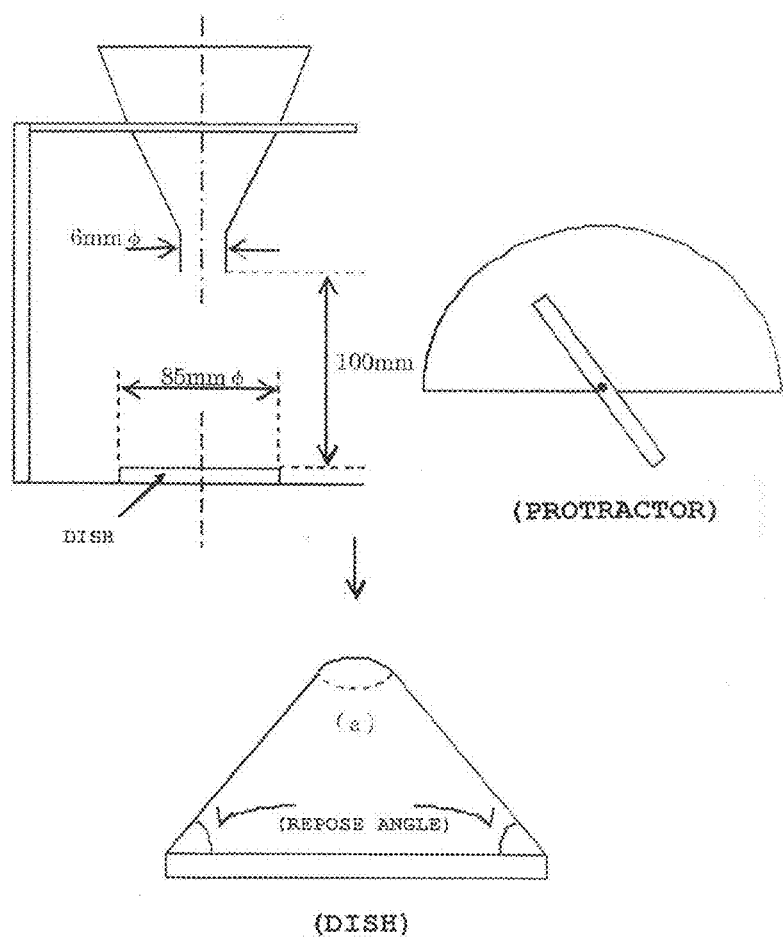
FIG. 3 shows constitution diagrams of a repose angle measuring apparatus used for repose angle measurement in Examples, a protractor used therein and an electronic even balance.

1) A repose angle measuring apparatus, 2) a protractor and 3) an electronic even balance were constituted as shown in FIG. 3.

(2) Operations

1) On a dish, 80 g of a sample is naturally dropped through a funnel of the apparatus.
2) The vertical angle (a) of a circular cone formed on the dish is read with the protractor up to a digit of an integer.
3) This operation is repeated 3 times, and the average value of the vertical angle (a) of the circular cone is determined.

(3) Calculation

The repose angle is calculated by the following equation. The smaller repose angle shows more excellent fluidity.

$$A = (180 - a)/2$$

wherein A is the repose angle (degrees) and a is the vertical angle (degrees) of the circular cone.

<Measurement of Rate of Dissolution (Solubility in Water)>

In a 20-ml glass sample bottle (27 mm in outer diameter× 55 mm in depth), 1.00 g of a sodium p-styrenesulfonate powder (wet powder containing impurities and water) was accurately weighed in a temperature-controlled room of 25° C., and thereafter, 9.00 g of ion-exchanged water was quickly added thereto. Then, the sample bottle was turned upside down with a period of one cycle per second, and the time before dissolution of sodium p-styrenesulfonate was visually judged.

<Measurement of Whiteness and Yellowness of Sodium p-Styrenesulfonate with Color-Difference Meter>

After a color-difference meter (manufactured by Nippon Denshoku Industries Co., Ltd., C-106) was switched on and stabilized for 30 minutes, a light projection lens (30 mm in diameter) and a sample stand (30 mm in diameter) were attached thereto, and standard adjustment was performed. In a cell, 3.0 g of a sample was weighed, and a weight of 1 kg was placed thereon for 30 seconds. Thereafter, it was confirmed that there were no space and no wrinkles at a bottom portion of the cell. Measurement was made with the color-difference meter to read the whiteness (WI value) and the yellowness (YI value).

<Measurement of APHA values of Aqueous Sodium p-Styrenesulfonate and Aqueous Poly(Sodium p-Styrenesulfonate) Solutions>

After a color-difference meter (manufactured by Nippon Denshoku Industries Co., Ltd., C-106) was switched on and stabilized for 30 minutes, a measuring method was changed to transmission, and a light projection lens (30 mm in diameter) and a sample stand (30 mm in diameter) were attached thereto. A standard white plate and a 0-CAL plate were set, and zero calibration was performed. After water was poured in a square cell and standard calibration was performed, 15 wt % aqueous sodium p-styrenesulfonate solution and 15 wt % aqueous poly(sodium p-styrenesulfonate) solution samples were each transferred into the square cell, and set, followed by reading the APHA values (converted from a calibration curve prepared by using standard solutions having APHA values of 0 to 500).

<Hue Evaluation as Synthetic Starch for Clothing Ironing Agent>

A commercially available white polyester cotton blend fabric cut to a circular form having a diameter of 5 cm was dipped in a 15 wt % aqueous solution (in terms of pure component) of 15 wt % poly(sodium p-styrenesulfonate). After the solution was allowed to soak in the whole fabric, it was pulled up with tweezers, and the excess solution was removed therefrom by shaking. Thereafter, it was dried with an iron of 180° C. for 3 minutes (the iron was fixed without moving) to prepare a test piece. The hue of the test piece was analyzed visually and with the above-mentioned color-difference meter.

After the color-difference meter (manufactured by Nippon Denshoku Industries Co., Ltd., C-106) was switched on and stabilized for 30 minutes, a light projection lens (30 mm in diameter) and a sample stand (30 mm in diameter) were attached thereto, and standard adjustment was performed. After the sample fabric was fixed onto the back of the sample stand, the sample stand was covered with a black box to block the light from the outside, followed by measurement of the hue. The performance as a synthetic starch for a clothing ironing agent was simply judged from the YI value representing the yellowness and the b value representing a yellowish and bluish color.

<Hue Evaluation of Chloroprene Rubber Solution>

A 5 wt % toluene solution of chloroprene rubber was prepared, and the hue (yellowness) was evaluated by measuring the absorbance at a wavelength of 440 nm using a spectrophotometer U-1500 manufactured by Hitachi, Ltd. The smaller value shows the better pale color.

<Evaluation of Heat Aging Resistance of Hue>

After chloroprene rubber was heated in a Geer oven at 70° C. for 3 days, the hue of the solution was evaluated by the above-mentioned method.

<Measurement of GPC Molecular Weight and Monomer polymerization Conversion>

The monomer polymerization conversion and the molecular weight of sodium PSS were measured under the following conditions:

Model=LC-8020 manufactured by Tosoh Corporation (degasser: SD-8022, pump: DP-8020, column oven: CO-8020, ultraviolet-visible detector: UV-8020)

Column=TSK guardcolumn α+TSK gel α-6000+TSK gel α-3000

Eluent=a solution of a phosphate buffer solution (pH=7) and acetonitrile in a volume ratio of 9:1 (the above-mentioned phosphate buffer solution was prepared by dissolving 0.08 moles of $KH_2PO_4$ and 0.12 moles of $Na_2HPO_4$ in pure water to bring the total volume to 1 litter.)

Column temperature: 40° C., flow rate: 0.6 ml/min

Detector: UV detector (wavelength: 230 nm), injection amount: 100 μl

Calibration curve: prepared from peak top molecular weights of monodisperse poly(sodium p-styrenesulfonate) (3K, 15K, 41K, 300K, 1000K, 2350K, 5000K) manufactured by Sowa Science Corporation and the elution times.

Example 1

Production of High-Purity Sodium p-Styrenesulfonate and Sodium PSS, and Evaluation Example 1 as Synthetic Starch for Clothing Ironing Agent <Production of p-β-Bromoethylbenzenesulfonic Acid Reduced in Iron Content>

In a polypropylene beaker, 600 ml of a cation exchange resin (manufactured by Organo Corporation, Amberlite RB120 (one regenerated with hydrochloric acid)) and 400 g of a 73 wt % aqueous p-β-bromoethylbenzenesulfonic acid solution were collected, and slowly stirred using a Teflon (tetrafluoroethylene) stirring blade at ordinary temperature for 5 hours. Thereafter, the ion exchange resin was separated by filtration through a glass filter, and the concentration of a filtrate was adjusted with a rotary evaporator to obtain 350 g of a 70 wt % aqueous p-β-bromoethylbenzenesulfonic acid solution. The iron content in the aqueous solution was 0.34 μg/g.

Incidentally, an intermediate product obtained during a production process of sodium p-styrenesulfonate was used as p-β-bromoethylbenzenesulfonic acid.

<Production of High-Purity Sodium p-Styrenesulfonate>

A stainless steel reactor having a jacket and equipped with a stirrer was charged with 390 parts by weight of a 12% aqueous sodium hydroxide solution and 1.2 parts by weight of sodium nitrite, and the temperature was increased to 70° C. with stirring. This was maintained at 90° C., and 660 parts by weight of a 48% aqueous sodium hydroxide solution and 1,012 parts by weight of the 70 wt % aqueous p-β-bromoethylbenzenesulfonic acid solution obtained above were added dropwise thereto with stirring under a nitrogen atmosphere over 3 hours. A slurry of sodium p-styrenesulfonate crystals obtained was cooled to 30° C., followed by solid-liquid separation with a centrifuge to obtain 446 parts by weight of a wet cake of sodium p-styrenesulfonate.

The above-mentioned sodium p-styrenesulfonate had a purity of 88.8 wt %, a water content of 6.5 wt %, an iron content of 0.56 μg/g and a sodium bromide content of 2.00 wt %. The contents of organic impurities such as isomers were (a) 0.16%, (b) 0.43%, (c) 2.65%, (d) 0.04% and (e) 0.15% (the HPLC chart is shown in FIG. 1).

The above-mentioned sodium p-styrenesulfonate had a median diameter of 81 µm, a content of small particles less than 10.00 µm of 0.5%, a repose angle of 46 degrees and a dissolution time in water of 165 seconds.

The above-mentioned sodium p-styrenesulfonate had a WI value of 95.7, a YI value of 5.8 and an APHA value of a 15 wt % aqueous solution of 30, and showed an apparently excellent hue, as compared to a conventional product (Comparative Example 1).

<Production of High-Purity Poly(Sodium p-Styrenesulfonate)>

A 1-liter glass flask equipped with a reflux condenser tube, a nitrogen introducing pipe and a paddle type stirrer was charged with 100.00 g of pure water, followed by heating in an oil bath at 85° C. under a nitrogen atmosphere. An aqueous sodium p-styrenesulfonate solution (in which 240.00 g of high-purity sodium p-styrenesulfonate obtained above was dissolved in 824.00 g of pure water) separately prepared was added dropwise thereto over 86 minutes, and an aqueous initiator solution (in which 2.00 g of ammonium persulfate was dissolved in 121.00 g of pure water) was added dropwise thereto over 220 minutes to perform polymerization. After 3 hours from the initiation of polymerization, the oil bath temperature was increased to 90° C., and polymerization was further continued for 3 hours to obtain an aqueous poly(sodium p-styrenesulfonate) solution.

The number average molecular weight Mn of poly(sodium p-styrenesulfonate) determined by GPC was 170,000, and the weight average molecular weight Mw was 360,000. This polymer was designated as PSS-1.

The APHA value of a 15 wt % aqueous solution of the above-mentioned PSS-1 was 50, and showed an apparently excellent hue, as compared to the conventional product (Comparative Example 1). The difference in hue was also clear by visual observation.

<Hue Evaluation as Synthetic Starch for Clothing Ironing Agent>

The hue of the fabric soaked in a 15 wt % aqueous solution of the above-mentioned PSS-1 and dried with an iron was slightly superior to that of Comparative Example 1 in visual evaluation. The b value of the fabric was −5.4 (the b value of the original fabric was −6.8), and the YI value was −11.1 (the YI value of the original fabric was −13.7), resulting in showing a degree of blue, not yellow. However, there was shown the hue apparently close to that of the original fabric, as compared to Comparative Example 1. That is to say, the superiority in hue over the conventional product (Comparative Example 1) is clear, even when the amount of coating is small. The above evaluation results are summarized in Table 1.

Example 2

Production of High-Purity Sodium p-Styrenesulfonate and Sodium PSS, and Evaluation Example 2 as Synthetic Starch for Clothing Ironing Agent <Production of High-Purity Sodium p-Styrenesulfonate>

A stainless steel reactor having a jacket and equipped with a stirrer was charged with 1,000 g of high-purity sodium p-styrenesulfonate obtained in Example 1, 1 g of sodium nitrite, 20 g of sodium hydroxide and 950 g of pure water, followed by stirring at 60° C. for 1 hour under a nitrogen atmosphere. Then, after cooling to room temperature over 3 hours, solid-liquid separation was performed with a centrifuge to obtain 899 g of a wet cake of high-purity sodium p-styrenesulfonate.

The above-mentioned high-purity sodium p-styrene-sulfonate had a purity of 89.1 wt %, a water content of 8.2 wt %, an iron content of 0.58 µg/g and a sodium bromide content of 0.20 wt %. The contents of organic impurities such as isomers were (a) 0.05%, (b) 0.00%, (c) 1.34%, (d) 0.01% and (e) 0.01%.

The above-mentioned sodium p-styrenesulfonate had a median diameter of 63 µm, a content of small particles less than 10.00 µm of 2.0%, a repose angle of 49 degrees and a dissolution time in water of 155 seconds.

The above-mentioned sodium p-styrenesulfonate had a WI value of 95.5, a YI value of 2.9 and an APHA value of a 15 wt % aqueous solution of 15, and showed an apparently excellent hue, as compared to the conventional product (Comparative Example 1). Further, it is clear that the hue is more improved by decreasing sodium bromide and impurities such as isomers, even when the iron content is the same level as that of Example 1, although the reason for this is not clear.

<Production of High-Purity Poly(Sodium p-Styrenesulfonate)>

A 1-liter glass flask equipped with a reflux condenser tube, a nitrogen introducing pipe and a paddle type stirrer was charged with 100.00 g of pure water, followed by heating in an oil bath at 85° C. under a nitrogen atmosphere. An aqueous sodium p-styrenesulfonate solution (in which 240.00 g of sodium p-styrenesulfonate obtained above was dissolved in 824.00 g of pure water) separately prepared was added dropwise thereto over 86 minutes, and an aqueous initiator solution (in which 2.00 g of 2,2'-azobis(2-amidinopropane) dihydrochloride was dissolved in 120.00 g of pure water) was added dropwise thereto over 220 minutes to perform polymerization. After 3 hours from the initiation of polymerization, the oil bath temperature was increased to 90° C., and polymerization was further continued for 3 hours to obtain an aqueous poly(sodium p-styrenesulfonate) solution.

The number average molecular weight Mn of poly(sodium p-styrenesulfonate) determined by GPC was 160,000, and the weight average molecular weight Mw was 350,000. This polymer was designated as PSS-2.

The APHA value of a 15 wt % aqueous solution of the above-mentioned PSS-2 was 10. It is clear that this has an excellent hue, as compared to the conventional product (Comparative Example 1).

<Hue Evaluation as Synthetic Starch for Clothing Ironing Agent>

The hue of the fabric soaked in a 15 wt % aqueous solution of the above-mentioned PSS-2 and dried with an iron was slightly superior to that of Comparative Example 1 in visual evaluation. The b value of the fabric was −6.0 (the b value of the original fabric was −6.8), and the YI value was −12.2 (the YI value of the original fabric was −13.7), resulting in showing a degree of blue, not yellow. However, there was shown a hue apparently close to that of the original fabric, as compared to Comparative Example 1. That is to say, the superiority in hue over the conventional product (Comparative Example 1) is clear, even when the amount of coating is small. The above evaluation results are summarized in Table 1.

Example 3

Production of Sodium PSS and Chloroprene Rubber and Evaluation Example 1

<Production of Poly(Sodium p-Styrenesulfonate)>

A 1-liter glass flask equipped with a reflux condenser tube, a nitrogen introducing pipe and a paddle type stirrer was charged with 84.00 g of pure water, followed by heating in an oil bath at 85° C. under a nitrogen atmosphere. An aqueous sodium p-styrenesulfonate solution (in which 193.00 g of sodium p-styrenesulfonate obtained in Example 1 and 8.56 g of thioglycerol were dissolved in 700.00 g of pure water) separately prepared was added dropwise thereto over 73 minutes, and an aqueous initiator solution (in which 5.10 g of 2,2'-azobis(2-amidinopropane) dihydrochloride was dissolved in 104.00 g of pure water) was added dropwise thereto over 130 minutes to perform polymerization. After 3 hours from the initiation of polymerization, the oil bath temperature was increased to 90° C., and polymerization was further continued for 3 hours to obtain an aqueous poly(sodium p-styrenesulfonate) solution.

The number average molecular weight Mn of poly(sodium p-styrenesulfonate) determined by GPC was 4,000, and the weight average molecular weight Mw was 5,200. This polymer was designated as PSS-3.

The APHA value of a 15 wt % aqueous solution of the above-mentioned PSS-3 was 15. It is clear that this has an excellent hue, as compared to the conventional product (Comparative Example 1).

<Production of Chloroprene Rubber>

A 10-liter stainless steel reactor having a jacket and equipped with a stirrer was charged with 100 parts by weight of chloroprene, 0.12 parts by weight of n-dodecyl mercaptan, 3.00 parts by weight of disproportionated potassium rosinate, 2.00 parts by weight of the above-mentioned poly(sodium p-styrenesulfonate), 0.20 parts by weight of sodium hydroxide, 0.005 parts by weight of sodium hydrosulfite and 100 parts by weight of pure water, and stirring was started under a nitrogen atmosphere. Polymerization was initiated at 12° C. while continuously adding dropwise a 0.35 wt % aqueous potassium persulfate solution. At the time when the polymerization conversion rate reached 70%, 0.05 parts by weight of 2,2'-methylenebis(4-ethyl-6-t-butylphenol) was added as a polymerization terminator to terminate the polymerization. No aggregates were observed at all in an emulsion.

After unreacted chloroprene was removed by a steam stripping process, the pH of the emulsion was adjusted to 6 with dilute acetic acid, followed by freezing coagulation, water washing and hot air drying to obtain 71 parts by weight of solid chloroprene rubber.

<Evaluation of Chloroprene Rubber>

The absorbance (hue) of the chloroprene rubber solution was 0.03, and the absorbance after heat aging resistance was 0.04. The results were apparently superior to those of Comparative Example 5. The above evaluation results are summarized in Table 1.

Example 4

Production of Sodium PSS and Chloroprene Rubber and Evaluation Example 2

<Production of Poly(Sodium p-Styrenesulfonate)>

A 1-liter glass flask equipped with a reflux condenser tube, a nitrogen introducing pipe and a paddle type stirrer was charged with 120.00 g of pure water, followed by heating in an oil bath at 85° C. under a nitrogen atmosphere. An aqueous sodium p-styrenesulfonate solution (in which 210.00 g of sodium p-styrenesulfonate obtained in Example 2, 19.98 g of methacrylic acid, 6.21 g of thioglycerol and 23.98 g of a 39.45 wt % aqueous sodium hydroxide solution were dissolved in 850.00 g of pure water) separately prepared was added dropwise thereto over 85 minutes, and an aqueous initiator solution (in which 3.33 g of 2,2'-azobis(2-amidinopropane) dihydrochloride was dissolved in 120.00 g of pure water) was added dropwise thereto over 140 minutes to perform polymerization. After 3 hours from the initiation of polymerization, the oil bath temperature was increased to 90° C., and polymerization was further continued for 3 hours to obtain an aqueous solution of a poly(sodium p-styrenesulfonate)/sodium methacrylate copolymer as sodium PSS.

The number average molecular weight Mn of the Poly (Sodium p-Styrenesulfonate)/sodium methacrylate copolymer determined by GPC was 5,600, and the weight average molecular weight Mw was 8,900. This polymer was designated as PSS-4.

The APHA value of a 15 wt % aqueous solution of the above-mentioned PSS-4 was 10. It is clear that this has an excellent hue, as compared to the conventional product (Comparative Example 1). Further, it is clear that the hue is more improved by decreasing sodium bromide and impurities such as isomers, even when the iron content is the same level as that of Example 3, although the reason for this is not clear.

<Production of Chloroprene Rubber>

A 10-liter stainless steel reactor having a jacket and equipped with a stirrer was charged with 100 parts by weight of chloroprene, 0.12 parts by weight of n-dodecyl mercaptan, 3.00 parts by weight of disproportionated potassium rosinate, 2.00 parts by weight of the above-mentioned poly(sodium p-styrenesulfonate)/sodium methacrylate copolymer, 0.20 parts by weight of sodium hydroxide, 0.005 parts by weight of sodium hydrosulfite and 100 parts by weight of pure water, and stirring was started under a nitrogen atmosphere. Polymerization was initiated at 12° C. while continuously adding dropwise a 0.35 wt % aqueous potassium persulfate solution. At the time when the polymerization conversion rate reached 70%, 0.05 parts by weight of 2,2'-methylenebis(4-ethyl-6-t-butylphenol) was added as a polymerization terminator to terminate the polymerization. No aggregates were observed at all in an emulsion.

After unreacted chloroprene was removed by a steam stripping process, the pH of the emulsion was adjusted to 6 with dilute acetic acid, followed by freezing coagulation, water washing and hot air drying to obtain 71 parts by weight of solid chloroprene rubber.

<Evaluation of Chloroprene Rubber>

The absorbance (hue) of the chloroprene rubber solution was 0.03, and the absorbance after heat aging resistance was 0.04. The results were apparently superior to those of Comparative Example 5. The above evaluation results are summarized in Table 1.

Example 5

Production of High-Purity Sodium p-Styrenesulfonate and Sodium PSS, and Evaluation Example 3 as Synthetic Starch for Clothing Ironing Agent <Production of High-Purity Sodium p-Styrenesulfonate>

A stainless steel reactor having a jacket and equipped with a stirrer was charged with 1,000 g of commercially available sodium p-styrenesulfonate (water content: 10.4 wt %, iron content: 5.12 µg/g, sodium bromide: 2.30 wt %, organic impurities such as isomers: (a) 0.38%, (b) 3.87%, (c) 7.77%, (d) 0.06% and (e) 0.73%), 1 g of sodium nitrite, 20 g of sodium hydroxide and 950 g of pure water, followed by stirring at 40° C. for 1 hour under a nitrogen atmosphere. Then, after cooling to room temperature for 30 minutes, solid-liquid separation was performed with a centrifuge to obtain 900 g of a wet cake of high-purity sodium p-styrenesulfonate.

The above-mentioned high-purity sodium p-styrene-sulfonate had a purity of 83.4 wt %, a water content of 10.2 wt %, an iron content of 1.03 μg/g and a sodium bromide content of 2.00 wt %. The contents of organic impurities such as isomers were (a) 0.30%, (b) 3.20%, (c) 6.40%, (d) 0.04% and (e) 0.39%.

The above-mentioned sodium p-styrenesulfonate had a median diameter of 18.6 μm, a content of small particles less than 10.00 μm of 14.3%, a repose angle of 59 degrees and a dissolution time in water of 130 seconds.

The above-mentioned sodium p-styrenesulfonate had a WI value of 95.0, a YI value of 7.5 and an APHA value of a 15 wt % aqueous solution of 80, and showed an apparently excellent hue, as compared to the conventional product (Comparative Example 1), although inferior to Examples 1 and 2. Further, it is clear that the hue is more improved by decreasing sodium bromide and impurities such as isomers, even when the iron content is equivalent to that of Comparative Example 5, although the reason for this is not clear.

<Production of High-Purity Poly(Sodium p-Styrenesulfonate)>

A 1-liter glass flask equipped with a reflux condenser tube, a nitrogen introducing pipe and a paddle type stirrer was charged with 100.00 g of pure water, followed by heating in an oil bath at 85° C. under a nitrogen atmosphere. An aqueous sodium p-styrenesulfonate solution (in which 240.00 g of high-purity sodium p-styrenesulfonate obtained above was dissolved in 824.00 g of pure water) separately prepared was added dropwise thereto over 86 minutes, and an aqueous initiator solution (in which 2.00 g of ammonium persulfate was dissolved in 121.00 g of pure water) was added dropwise thereto over 220 minutes to perform polymerization. After 3 hours from the initiation of polymerization, the oil bath temperature was increased to 90° C., and polymerization was further continued for 3 hours to obtain an aqueous poly(sodium p-styrenesulfonate) solution.

The number average molecular weight Mn of poly(sodium p-styrenesulfonate) determined by GPC was 160,000, and the weight average molecular weight Mw was 340,000. This polymer was designated as PSS-5.

The APHA value of a 15 wt % aqueous solution of the above-mentioned PSS-5 was 100. It is clear that this has an excellent hue, as compared to Comparative Example 1.

<Hue Evaluation as Synthetic Starch for Clothing Ironing Agent>

The hue of the fabric soaked in a 15 wt % aqueous solution of the above-mentioned PSS-5 and dried with an iron was slightly superior to that of Comparative Example 1 in visual evaluation. The b value of the fabric was −4.9 (the b value of the original fabric was −6.8), and the YI value was −10.0 (the YI value of the original fabric was −13.7), resulting in showing a degree of blue, not yellow. However, there was shown a hue apparently close to that of the original fabric, as compared to Comparative Example 1. That is to say, the superiority in hue over Comparative Example 1 is clear, even when the amount of coating is small. The above evaluation results are summarized in Table 1.

Comparative Example 1

Production of Sodium PSS, and Evaluation Example 4 as Synthetic Starch for Clothing Ironing Agent <Production of Poly(Sodium p-Styrenesulfonate)>

Figure 2:
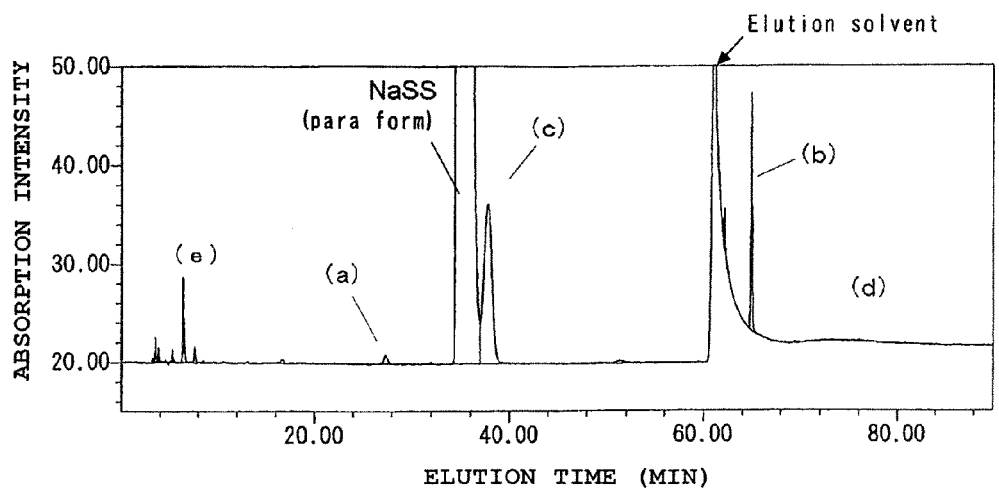
FIG. 2 shows HPLC chromatogram of low-purity sodium p-styrenesulfonate of Comparative Example 1. The others are the same as the description of FIG. 1.

As a result of analysis of commercially available sodium p-styrenesulfonate A, the purity was 82.9 wt %, the water content was 10.4 wt %, the iron content was 5.12 μg/g, and the sodium bromide content was 2.30 wt %. The contents of organic impurities such as isomers were (a) 0.38%, (b) 3.87%, (c) 7.77%, (d) 0.06% and (e) 0.62% (the HPLC chart is shown in FIG. 2). Further, the WI value was 90.2, the YI value was 16.5, and the APHA value of a 15 wt % aqueous solution was 220. This was apparently inferior in hue to high-purity sodium p-styrenesulfonate of Example 1.

The above-mentioned sodium p-styrenesulfonate had a median diameter of 20.2 μm, a content of small particles less than 10.00 μm of 12.6%, a repose angle of 60 degrees and a dissolution time in water of 132 seconds.

Using the above-mentioned sodium p-styrenesulfonate, poly(sodium p-styrenesulfonate) was synthesized under the same conditions as in Example 1. The number average molecular weight Mn determined by GPC was 160,000, and the weight average molecular weight Mw was 350,000. This polymer was designated as PSS-6.

The APHA value of a 15 wt % aqueous solution of the above-mentioned PSS-6 was 250, and this was apparently inferior as compared to sodium p-styrenesulfonate as a raw material and poly(sodium p-styrenesulfonate) of Example 1.

The hue of the fabric soaked in a 15 wt % aqueous solution of the above-mentioned PSS-6 and dried with an iron was slightly inferior to that of Example 1 in visual evaluation. The b value of the fabric was −3.8 (the b value of the original fabric was −6.8), and the YI value was −8.3 (the YI value of the original fabric was −13.7), resulting in showing a degree of blue, not yellow. However, there was shown a hue apparently away from that of the original fabric, as compared to Example 1. That is to say, the inferiority in hue to Example 1 is clear, even when the amount of coating is small. The above evaluation results are summarized in Table 1.

Comparative Example 2

Production of Sodium PSS, and Evaluation Example 5 as Synthetic Starch for Clothing Ironing Agent Using the same commercially available sodium p-styrenesulfonate A as in Comparative Example 1, poly(sodium p-styrenesulfonate) was synthesized under the same conditions as in Example 2. The number average molecular weight Mn determined by GPC was 150,000, and the weight average molecular weight Mw was 340,000. This polymer was designated as PSS-7.

The APHA value of a 15 wt % aqueous solution of the above-mentioned PSS-7 was 210, and this was apparently inferior as compared to sodium p-styrenesulfonate as a raw material and poly(sodium p-styrenesulfonate) of Example 2.

It is clear herein that a sufficient hue is not obtained, when the p-styrenesulfonate as the raw material contains specific impurities, even in the case of using the azo initiator, 2,2'-azobis(2-amidinopropane) dihydrochloride, which is reported to have no adverse influence on the hue of poly (sodium p-styrenesulfonate), namely to provide a good hue (for example, JP-A-11-181004).

The hue of the fabric soaked in a 15 wt % aqueous solution of the above-mentioned PSS-7 and dried with an iron was slightly inferior to that of Example 2 in visual evaluation. The b value of the fabric was −4.2 (the b value of the original fabric was −6.8), and the YI value was −8.8 (the YI value of the original fabric was −13.7), resulting in showing a degree of blue, not yellow. However, there was shown a hue apparently away from that of the original fabric, as compared to Example 2. That is to say, the inferiority in hue to Example 2 is clear, even when the amount of coating is small. The above evaluation results are summarized in Table 1.

Comparative Example 3

Production of Sodium PSS, and Evaluation Example 6 as Synthetic Starch for Clothing Ironing Agent <Production of Poly(Sodium p-Styrenesulfonate)>

A stainless steel reactor having a jacket and equipped with a stirrer was charged with 1,500 g of the same commercially available sodium p-styrenesulfonate A as in Comparative Examples 1 and 2, 3.0 g of sodium nitrite and 10,800 g of isopropanol, followed by stirring and dispersing. Thereafter, 2,700 g of pure water was added thereto, followed by stirring at 70° C. for 1 hour under a nitrogen atmosphere. Then, after cooling to room temperature over 4 hours, Nutsche filtration was performed, and further, the solvent was removed with a centrifuge to obtain 1,370 g of a wet cake of sodium p-styrenesulfonate.

As a result of analysis of the above-mentioned purified sodium p-styrenesulfonate, the purity was 85.5 wt %, the water content was 10.8 wt %, the iron content was 5.10 µg/g and the sodium bromide content was 0.45 wt %. The contents of organic impurities such as isomers were (a) 0.01%, (b) 0.01%, (c) 1.60%, (d) 0.03% and (e) 0.03%. As a result of measurement of the hue, the WI value was 93.5, the YI value was 12.5, and the APHA value of a 15 wt % aqueous solution was 150. This was apparently inferior in hue to high-purity sodium p-styrenesulfonate of Example 1. That is to say, it is clear that the sufficient hue is not obtained when iron is contained in large amounts, even in the case of reducing sodium bromide and organic impurities such as isomers.

The above-mentioned sodium p-styrenesulfonate had a median diameter of 21.5 µm, a content of small particles less than 10.00 µm of 12.1%, a repose angle of 59 degrees and a dissolution time in water of 123 seconds.

Using the above-mentioned sodium p-styrenesulfonate, poly(sodium p-styrenesulfonate) was synthesized under the same conditions as in Example 1. The number average molecular weight Mn determined by GPC was 180,000, and the weight average molecular weight Mw was 380,000. This polymer was designated as PSS-8.

The APHA value of a 15 wt % aqueous solution of the above-mentioned PSS-8 was 170, and this was apparently inferior as compared to poly(sodium p-styrenesulfonate) of Example 1. Further, it is clear that when iron is contained in sodium p-styrenesulfonate in large amounts, the APHA after conversion to the polymer is also largely increased.

<Evaluation as Synthetic Starch for Clothing Ironing Agent>

The hue of the fabric soaked in a 15 wt % aqueous solution of the above-mentioned PSS-8 and dried with an iron was slightly inferior to that of Example 1 in visual evaluation. The b value of the fabric was −4.5 (the b value of the original fabric was −6.8), and the YI value was −8.9 (the YI value of the original fabric was −13.7), resulting in showing a degree of blue, not yellow. However, there was shown a hue apparently away from that of the original fabric, as compared to Example 1. That is to say, the inferiority in hue to Example 1 is clear, even when the amount of coating is small. The above evaluation results are summarized in Table 1.

Comparative Example 4

Production of Sodium p-Styrenesulfonate and Sodium PSS, and Evaluation Example 7 as Synthetic Starch for Clothing Ironing Agent <Production of Sodium p-Styrenesulfonate>

A stainless steel reactor having a jacket and equipped with a stirrer was charged with 1,054 parts by weight of a 35% aqueous sodium hydroxide solution and 1.2 parts by weight of sodium nitrite, and the temperature was increased to 105° C. with stirring. This was maintained at 105° C., and 1,012 parts by weight of the 70 wt % aqueous p-β-bromoethyl-benzenesulfonic acid solution obtained in Example 1 was added dropwise thereto with stirring under a nitrogen atmosphere over 1 hour. A slurry of sodium p-styrenesulfonate crystals obtained was cooled to 30° C., followed by solid-liquid separation with a centrifuge to obtain 451 parts by weight of a wet cake of sodium p-styrenesulfonate.

As a result of analysis of the above-mentioned sodium p-styrenesulfonate, the purity was 82.7 wt %, the water content was 10.5 wt %, the iron content was 1.05 µg/g and the sodium bromide content was 2.51 wt %. The contents of organic impurities such as isomers were (a) 0.40%, (b) 4.20%, (c) 8.20%, (d) 0.10% and (e) 0.72%. Further, the WI value was 93.0, the YI value was 10.1, and the APHA value of a 15 wt % aqueous solution was 120. This was apparently inferior to high-purity sodium p-styrenesulfonate of Example 1. That is to say, it is clear that a sufficient hue is not obtained when sodium bromide and organic impurities such as isomers are contained in large amounts, even in the case where the iron content in sodium p-styrenesulfonate is less than 3.00 µg/g.

The above-mentioned sodium p-styrenesulfonate had a median diameter of 20.6 µm, a content of small particles less than 10.00 µm of 14.3%, a repose angle of 60 degrees and a dissolution time in water of 126 seconds.

<Production of Poly(Sodium p-Styrenesulfonate)>

Using the above-mentioned sodium p-styrenesulfonate, poly(sodium p-styrenesulfonate) was synthesized under the same conditions as in Example 1. The number average molecular weight Mn determined by GPC was 160,000, and the weight average molecular weight Mw was 350,000. This polymer was designated as PSS-9.

The APHA value of a 15 wt % aqueous solution of the above-mentioned PSS-9 was 150, and this was apparently inferior in hue as compared to poly(sodium p-styrenesulfonate) of Example 1. Further, it is clear that when sodium bromide and organic impurities such as isomers are contained in sodium p-styrenesulfonate in large amounts, the APHA after conversion to the polymer is also largely increased.

<Evaluation as Synthetic Starch for Clothing Ironing Agent>

The hue of the fabric soaked in a 15 wt % aqueous solution of the above-mentioned PSS-9 and dried with an iron was slightly inferior to that of Example 1 in visual evaluation. The b value of the fabric was −4.3 (the b value of the original fabric was −6.8), and the YI value was −8.7 (the YI value of the original fabric was −13.7), resulting in showing a degree of blue, not yellow. However, there was shown a hue apparently away from that of the original fabric, as compared to Example 1. That is to say, the inferiority in hue to Example 1 is clear, even when the amount of coating is small. The above evaluation results are summarized in Table 1.

Comparative Example 5

Production of Sodium PSS and Chloroprene Rubber, and Evaluation Example 3

<Production of Poly(Sodium p-Styrenesulfonate)>

An aqueous poly(sodium p-styrenesulfonate)/sodium methacrylate copolymer was synthesized under the same conditions as in Example 4 with the exception that commercially available sodium p-styrenesulfonate used in Comparative Example 1 was used instead of high-purity sodium p-styrenesulfonate used in Example 4.

The number average molecular weight Mn of the poly (sodium p-styrenesulfonate)/sodium methacrylate copolymer determined by GPC was 5,300, and the weight average molecular weight Mw was 9,100. This polymer was designated as PSS-10.

The APHA value of a 15 wt % aqueous solution of the above-mentioned PSS-10 was 210, and this was apparently inferior in hue as compared to the poly(sodium p-styrenesulfonate)/sodium methacrylate copolymer of Example 4.

<Production of Chloroprene Rubber>

Chloroprene rubber (71 parts by weight) was obtained under the same conditions as in Example 4 with the exception that the sodium p-polystyrenesulfonic acid/sodium methacrylate copolymer obtained above was used instead of the sodium p-polystyrenesulfonic acid/sodium methacrylate copolymer used in Example 4.

<Evaluation of Chloroprene Rubber>

The absorbance (hue) of the chloroprene rubber solution was 0.15, and the absorbance after heat aging resistance was 0.19. The results were apparently inferior to those of Example 4. The above evaluation results are summarized in Table 1.

Comparative Example 6

Production of Sodium PSS, and Evaluation Example 8 as Synthetic Starch for Clothing Ironing Agent <Production of Poly(Sodium p-Styrenesulfonate)>

As a result of analysis of commercially available sodium p-styrenesulfonate B, the purity was 82.3 wt %, the water content was 10.3 wt %, the iron content was 2.90 µg/g and the sodium bromide content was 2.40 wt %. The contents of organic impurities such as isomers were (a) 0.35%, (b) 4.20%, (c) 7.90%, (d) 0.05% and (e) 0.61%. Further, the WI value was 91.0, the YI value was 16.0, and the APHA value of a 15 wt % aqueous solution was 200. This was apparently inferior in hue to high-purity sodium p-styrenesulfonate of Example 1.

The above-mentioned sodium p-styrenesulfonate had a median diameter of 21.3 µm, a content of small particles less than 10.00 µm of 12.7%, a repose angle of 59 degrees and a dissolution time in water of 122 seconds.

Using the above-mentioned sodium p-styrenesulfonate, poly(sodium p-styrenesulfonate) was synthesized under the same conditions as in Example 1. The number average molecular weight Mn determined by GPC was 160,000, and the weight average molecular weight Mw was 350,000. This polymer was designated as PSS-11.

The APHA value of a 15 wt % aqueous solution of the above-mentioned PSS-11 was 230, and this was apparently inferior as compared to sodium p-styrenesulfonate as a raw material and poly(sodium p-styrenesulfonate) of Example 1.

The hue of the fabric soaked in a 15 wt % aqueous solution of the above-mentioned PSS-11 and dried with an iron was slightly inferior to that of Example 1 in visual evaluation. The b value of the fabric was −4.2 (the b value of the original fabric was −6.8), and the YI value was −8.8 (the YI value of the original fabric was −13.7), resulting in showing a degree of blue, not yellow. However, there was shown a hue apparently away from that of the original fabric, as compared to Example 1. That is to say, the inferiority in hue to Example 1 is clear, even when the amount of coating is small. The above evaluation results are summarized in Table 1.

TABLE 1

| | | Example 1 | Example 2 | Example 3 | Example 4 | Example 5 | Comparative Example 1 | Comparative Example 2 | Comparative Example 3 | Comparative Example 4 | Comparative Example 5 | Comparative Example 6 |
|---|---|---|---|---|---|---|---|---|---|---|---|---|
| [Properties of sodium p-styrene-sulfonate] | | | | | | | | | | | | |
| Median diameter | μm | 81.0 | 63.0 | The same as Example 1 | The same as Example 2 | 18.6 | 20.2 | The same as Comparative Example 1 | 21.5 | 20.6 | The same as Comparative Example 1 | 21.3 |
| Small particles less than 10.00 μm | % | 0.5 | 2.0 | | | 14.3 | 12.6 | | 12.1 | 14.3 | | 12.7 |
| Repose angle | deg | 46 | 49 | | | 59 | 60 | | 59 | 60 | | 59 |
| Rate of dissolution | sec | 165 | 155 | | | 130 | 132 | | 123 | 126 | | 122 |
| [Purity of sodium p-styrenesulfonate] | | | | | | | | | | | | |
| Pure content | wt % | 88.8 | 89.1 | | | 83.4 | 82.9 | | 85.5 | 82.7 | | 82.3 |
| Water content | wt % | 6.5 | 8.2 | | | 10.2 | 10.4 | | 10.8 | 10.5 | | 10.3 |
| Iron content | μg/g | 0.56 | 0.58 | | | 1.03 | 5.12 | | 5.10 | 1.05 | | 2.90 |
| Sodium bromide | wt % | 2.00 | 0.20 | | | 2.00 | 2.30 | | 0.45 | 2.51 | | 2.40 |
| Organic impurities | %[3] | | | | | | | | | | | |
| (a) Sodium o-styrenesulfonate | | 0.16 | 0.05 | | | 0.30 | 0.38 | | 0.01 | 0.40 | | 0.35 |
| (b) Sodium p-β-bromoethylbenzene-sulfonate | | 0.43 | 0.00 | | | 3.20 | 3.87 | | 0.01 | 4.20 | | 4.20 |
| (c) Sodium m-styrenesulfonate | | 2.65 | 1.34 | | | 6.40 | 7.77 | | 1.60 | 8.20 | | 7.90 |
| (d) Sodium bromostyrenesulfonate | | 0.04 | 0.01 | | | 0.04 | 0.06 | | 0.03 | 0.10 | | 0.05 |
| (e) Sodium p-β-hydroxyethylbenzene-sulfonate | | 0.15 | 0.01 | | | 0.39 | 0.62 | | 0.03 | 0.72 | | 0.61 |
| [Hue of sodium p-styrenesulfonate] | | | | | | | | | | | | |
| Whiteness (WI value) | | 95.7 | 95.5 | The same as Example 1 | The same as Example 2 | 95.0 | 90.2 | The same as Comparative Example 1 | 93.5 | 93.00 | The same as Comparative Example 1 | 91.0 |
| Yellowness (YI value) | | 5.8 | 2.9 | | | 7.5 | 16.5 | | 12.5 | 10.1 | | 16.0 |
| Solution APHA value | | 30 | 15 | | | 80 | 220 | | 150 | 120 | | 200 |
| [Hue of poly(sodium p-styrenesulfonate)] | | | | | | | | | | | | |
| Kind of polymerization initiator[1] | | APS | V-50 | V-50 | V-50 | APS | APS | V-50 | APS | APS | V-50 | APS |
| Solution APHA value | | 50 | 10 | 15 | 10 | 100 | 250 | 210 | 170 | 150 | 210 | 230 |
| [Evaluation as ironing agent (hue of fabric)][2] | | | | | | | | | | | | |
| YI value | | −11.1 | −12.2 | — | — | −10.0 | −8.3 | −8.8 | −8.9 | −8.7 | −8.8 | −8.8 |
| b value | | −5.4 | −6.0 | — | — | −4.9 | −3.8 | −4.2 | −4.5 | −4.3 | −4.2 | −4.2 |
| [Evaluation as chloroprene rubber dispersant] | | | | | | | | | | | | |
| Hue of original rubber solution (absorbance) | | — | — | 0.03 | 0.03 | — | — | — | — | — | 0.15 | — |
| Hue of rubber solution after heat aging resistance (absorbance) | | — | — | 0.04 | 0.04 | — | — | — | — | — | 0.19 | — |

[1] APS = ammonium persulfate, V-50 = 2,2′-azobis(2-amidinopropane) dihydrochloride
[2] YI value of the original fabric soaked in nothing = −13.7, b value = −6.8
[3] The area ratio at the time when the sum of HPLC peak areas of (a) to (e) and sodium p-styrenesulfonate is taken as 100

Example 6

A stainless steel reactor having a jacket and equipped with a stirrer was charged with 750 kg of a 11.7 wt % aqueous sodium hydroxide solution and 2.5 kg of sodium nitrite, and heated up to 90° C. At that temperature, 2,000 kg of a 73 wt % aqueous p-β-bromoethylbenzenesulfonic acid solution obtained in the same manner as in Example 1 and 950 kg of a 48 wt % aqueous sodium hydroxide solution were separately introduced at a constant rate over 4 hours (the sodium hydroxide concentration in the reactor gradually increased from 11.66 wt % at the start of the reaction to 14.69 wt % after 4 hours from the start of the reaction (at the end of the reaction), and the p-β-bromoethylbenzenesulfonic acid concentration gradually increased from 0.00 wt % at the start of the reaction to 39.43 wt % after 4 hours from the start of the reaction (at the end of the reaction)), followed by reaction crystallization of sodium p-styrenesulfonate. A slurry thereof was cooled to 40° C. over 2 hours. Thereafter, solid-liquid separation was performed by centrifugation. Separation was extremely easy, and 940 kg of a high-purity wet cake having a sodium styrenesulfonate content of 88.5 wt % was obtained by shaking for 30 minutes. Using a uniaxial screw blender, this wet cake was forcedly fluidized at 40° C. and a rotational speed of 20 rpm for 60 minutes. Sodium p-styrenesulfonate obtained had a median diameter of 63.1 μm, a content of small particles less than 10.00 μm of 1.50%, a water content of 7.1 wt %, a repose angle of 47 degrees and a dissolution time in water of 160 seconds. This was slightly inferior in fluidity to Comparative Example 8, but far superior in solubility. It is therefore clear that this is excellent in the balance between fluidity and solubility.

Incidentally, the numerical values of sodium bromide and organic impurities such as isomers are as shown in Table 2.

Figure 4:
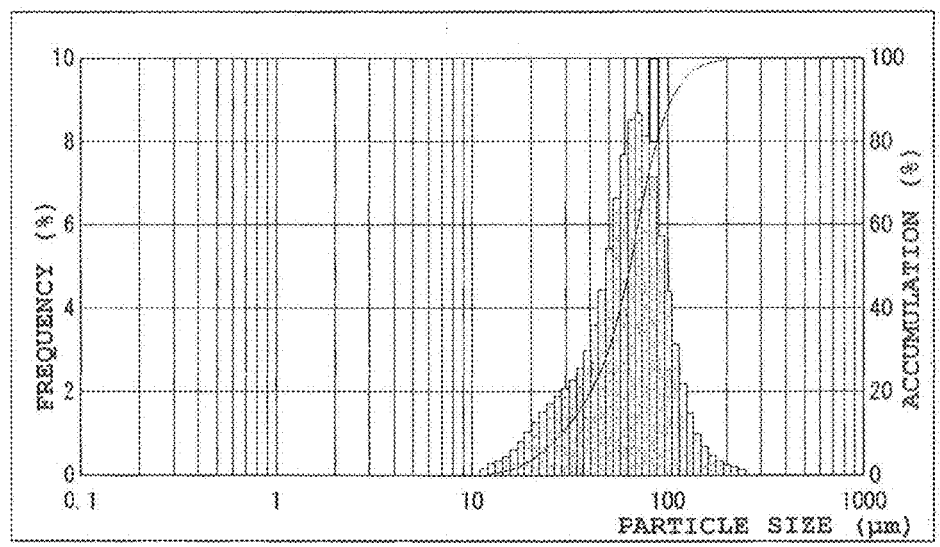
FIG. 4 shows a Microtrac particle size distribution of sodium p-styrenesulfonate of Example 6.
Figure 8:
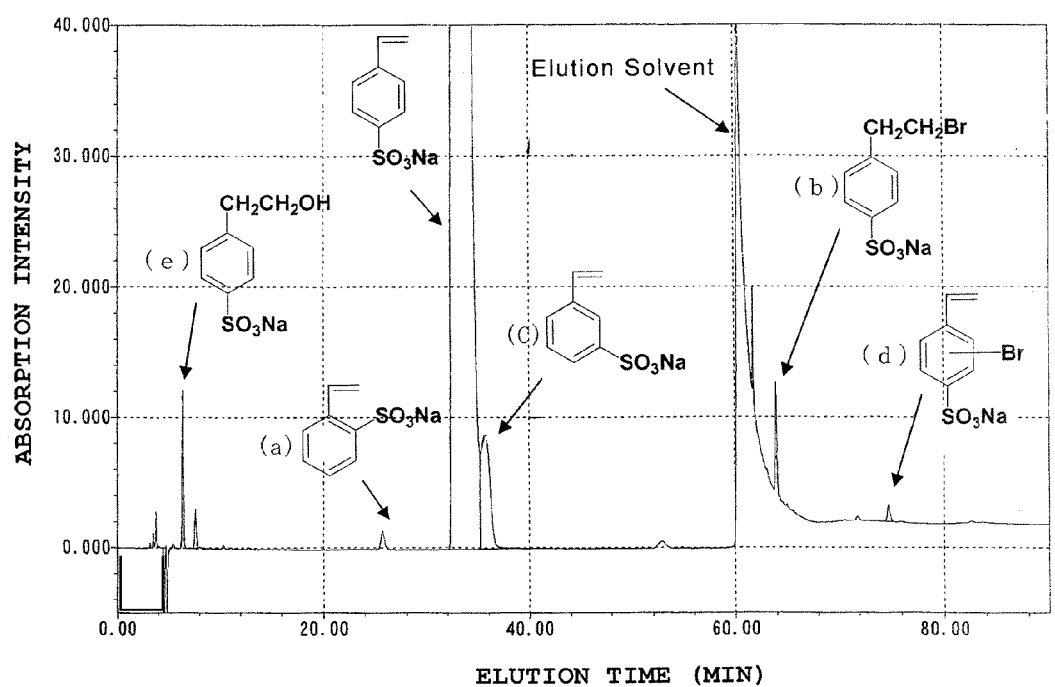
FIG. 8 shows HPLC chromatogram of sodium p-styrenesulfonate obtained in Example 6 (and used in Example 9).

Further, for sodium p-styrenesulfonate obtained in Example 6, a Microtrac particle size distribution is shown in FIG. 4, an electron microscope image is shown in FIG. 5, and HPLC chromatogram is shown in FIG. 8.

Example 7

Reaction crystallization of sodium p-styrenesulfonate was performed under the same conditions as in Example 6 with the exception that the aqueous p-β-bromoethylbenzenesulfonic acid solution and the aqueous sodium hydroxide solution were fed at the constant rate for 2.5 hours instead of being fed at the constant rate for 4 hours (the sodium hydroxide concentration in the reactor gradually increased from 11.66 wt % at the start of the reaction to 14.69 wt % after 2.5 hours from the start of the reaction (at the end of the reaction), and the p-β-bromoethylbenzenesulfonic acid concentration gradually increased from 0.00 wt % at the start of the reaction to 39.43 wt % after 2.5 hours from the start of the reaction (at the end of the reaction)). A slurry thereof was cooled to 40° C. over 2 hours. Thereafter, solid-liquid separation was performed by centrifugation. Separation was extremely easy, and 930 kg of a high-purity wet cake having a sodium styrene-sulfonate content of 88.9 wt % was obtained by shaking for 30 minutes. Using a uniaxial screw blender, this wet cake was forcedly fluidized at 40° C. and a rotational speed of 20 rpm for 60 minutes. Sodium p-styrenesulfonate obtained had a median diameter of 110 μm, a content of small particles less than 10.00 μm of 0.00%, a water content of 6.1 wt % and a repose angle of 43 degrees. The dissolution time in water was 200 seconds. It is clear that this is superior in the balance between fluidity and solubility as compared to Comparative Example 8. Incidentally, the numerical values of sodium bromide and organic impurities such as isomers are as shown in Table 2.

Example 8

Reaction crystallization of sodium p-styrenesulfonate was performed under the same conditions as in Example 6 with the exception that the aqueous p-β-bromoethylbenzenesulfonic acid solution and the aqueous sodium hydroxide solution were fed at the constant rate for 5 hours instead of being fed at the constant rate for 4 hours (the sodium hydroxide concentration in the reactor gradually increased from 11.66 wt % at the start of the reaction to 14.69 wt % after 5 hours from the start of the reaction (at the end of the reaction), and the p-β-bromoethylbenzenesulfonic acid concentration gradually increased from 0.00 wt % at the start of the reaction to 39.43 wt % after 5 hours from the start of the reaction (at the end of the reaction)). A slurry thereof was cooled to 40° C. over 2 hours. Thereafter, solid-liquid separation was performed by centrifugation. Separation was extremely easy, and 950 kg of a high-purity wet cake having a sodium styrene-sulfonate content of 88.9 wt % was obtained by shaking for 30 minutes. Using a uniaxial screw blender, this wet cake was forcedly fluidized at 40° C. and a rotational speed of 20 rpm for 60 minutes. Sodium p-styrenesulfonate obtained had a median diameter of 37 μm, a content of small particles less than 10.00 μm of 3.1%, a water content of 8.6 wt % and a repose angle of 51 degrees. The dissolution time in water was 140 seconds. This was slightly inferior in solubility as compared to Comparative Examples 7 and 9, but far superior in fluidity. It is therefore clear that this is excellent in the balance between fluidity and solubility.

Incidentally, the numerical values of sodium bromide and organic impurities such as isomers are as shown in Table 2.

Example 9

Purification

A stainless steel reactor having a jacket and equipped with a stirrer was charged with 1,000 g of sodium p-styrenesulfonate obtained in Example 6, 1.0 g of sodium nitrite, 20.0 g of sodium hydroxide and 950.0 g of pure water, followed by stirring at 40° C. for 1 hour under a nitrogen atmosphere. Then, after cooling to room temperature over 3 hours, solid-liquid separation was performed with a centrifuge to obtain 898.0 g of a wet cake of high-purity sodium p-styrenesulfonate.

Purified high-purity sodium p-styrenesulfonate obtained had a median diameter of 48 μm, a water content of 8.6 wt %, a repose angle of 50 degrees and a content of small particles less than 10.00 μm of 2.5%. The dissolution time in water was 130 seconds. This was slightly inferior in solubility as compared to Comparative Examples 7 and 9, but far superior in fluidity. It is therefore clear that this is excellent in the balance between fluidity and solubility.

Further, the above-mentioned sodium p-styrenesulfonate had a purity of 89.1 wt %, a water content of 8.6 wt % and a sodium bromide content of 0.20 wt %. The contents of organic impurities such as isomers were (a) 0.06%, (b) 0.03%, (c) 1.34%, (d) 0.10% and (e) 0.00%.

Incidentally, sodium p-styrenesulfonate before purification had a purity of 88.5 wt %, a water content of 7.1 wt % and a sodium bromide content of 2.10 wt %. The contents of organic impurities such as isomers were (a) 0.16%, (b) 0.43%, (c) 2.64%, (d) 0.12% and (e) 0.48% (provided that the sum of peak areas of sodium p-styrenesulfonate and (a) to (e) is 100). It is therefore clear that the degree of purification is high as compared to Comparative Example 9. The reason for this is considered to be that solid-liquid separation smoothly proceeded because of good centrifugal filterability.

Comparative Example 7

Sodium p-Styrenesulfonate Having Small Particle Size

Figure 6:
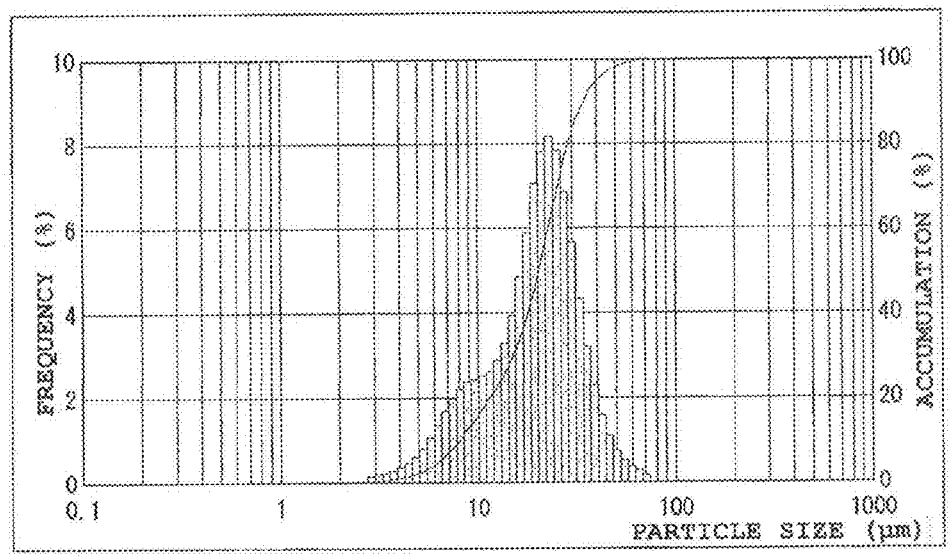
FIG. 6 shows a Microtrac particle size distribution of sodium p-styrenesulfonate of Comparative Example 7.
Figure 7:
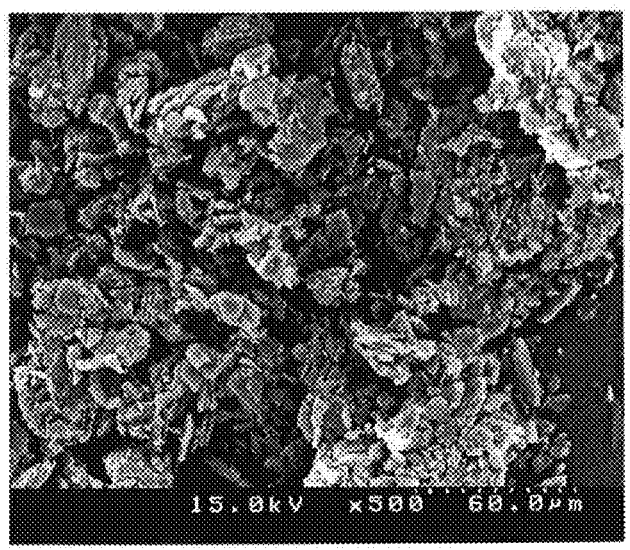
FIG. 7 shows a scanning electron microscope image (magnification: ×500) of sodium p-styrenesulfonate of Comparative Example 7.

As a result of analysis of commercially available sodium p-styrenesulfonate, the median diameter was 19.8 µm, the content of small particles less than 10.00 µm was 13.60% (a Microtrac particle size distribution is shown in FIG. 6, and an electron microscope image is shown in FIG. 7), the water content was 10.40 wt %, the repose angle was 59 degrees, and the dissolution time in water was 130 seconds. Further, the numerical values of sodium bromide and impurities such as organic impurities were as shown in Table 2. It is clear that this is inferior in fluidity and also has a high water content (the sodium p-styrenesulfonate content is low) as compared to Examples 8 and 9, although equivalent to or higher than Examples 8 and 9 in solubility.

Then, a stainless steel reactor having a jacket and equipped with a stirrer was charged with 1,000 g of the above-mentioned commercially available sodium p-styrenesulfonate, 1.0 g of sodium nitrite, 20.0 g of sodium hydroxide and 950.0 g of pure water, followed by stirring at 40° C. for 1 hour under a nitrogen atmosphere. Then, after cooling to room temperature over 3 hours, solid-liquid separation was performed with a centrifuge to obtain 897.0 g of a wet cake of high-purity sodium p-styrenesulfonate.

Purified high-purity sodium p-styrenesulfonate obtained had a median diameter of 22.3 µm, a water content of 10.8 wt %, a repose angle of 58 degrees and a content of small particles less than 10.00 µm of 3.1%. The dissolution time in water was 128 seconds (the results are summarized in Table 2).

Further, the above-mentioned sodium p-styrenesulfonate had a purity of 85.5 wt %, a water content of 10.8 wt % and a sodium bromide content of 1.10 wt %. The contents of organic impurities such as isomers were (a) 0.22%, (b) 2.80%, (c) 6.93%, (d) 0.05% and (e) 0.20%.

Incidentally, sodium p-styrenesulfonate before purification had a purity of 83.4 wt %, a water content of 10.4 wt % and a sodium bromide content of 2.10 wt %. The contents of organic impurities such as isomers were (a) 0.35%, (b) 3.46%, (c) 7.74%, (d) 0.06% and (e) 0.70% (provided that the sum of peak areas of sodium p-styrenesulfonate and (a) to (e) is 100). It is therefore clear that the degree of purification is low as compared to Example 9. The reason for this is considered to be that solid-liquid separation did not proceed smoothly because of poor centrifugal filterability.

Comparative Example 8

Sodium p-Styrenesulfonate Having Large Particle Size

Into a stainless steel reactor having a jacket and equipped with a stirrer, 179 kg of a 70 wt % aqueous p-β-bromoethylbenzenesulfonic acid solution and 203 kg of a 25 wt % aqueous sodium hydroxide solution (containing 0.2 wt % of sodium nitrite) were separately continuously introduced at a reaction temperature of 60° C. per hour, followed by reaction crystallization of sodium p-styrenesulfonate (the sodium hydrochloride concentration in the reactor was 13.29 wt % from the start of the reaction to 1 hour after the start of the reaction, and the p-β-bromoethylbenzenesulfonic acid concentration was also as high as 32.80 wt % from the start of the reaction to 1 hour after the start of the reaction). A crystal slurry was continuously taken out intermittently every 5 minutes in an amount of 382 kg per hour. The slurry was cooled to 40° C. over 2 hours, and solid-liquid separation was performed by centrifugation. A wet cake having a sodium styrenesulfonate concentration of 85.1 wt % was obtained by shaking for 30 minutes. Using a uniaxial screw blender, this wet cake was forcedly fluidized at 40° C. and a rotational speed of 20 rpm for 60 minutes. Sodium p-styrenesulfonate obtained had a median diameter of 160 µm, a content of small particles less than 10.00 µm of 0.00%, a water content of 5.9 wt % and a repose angle of 45 degrees. However, the dissolution time in water was 270 seconds. It is therefore clear that this is inferior in solubility as compared to Examples 6 and 7. Incidentally, the numerical values of sodium bromide and organic impurities such as isomers are as shown in Table 2.

Comparative Example 9

A stainless steel reactor having a jacket and equipped with a stirrer was charged with 1,054 kg of a 35 wt % aqueous sodium hydroxide solution and 1.2 kg of sodium nitrite, and heated to 90° C. Then, 1,012 kg of a 70 wt % aqueous p-β-bromoethylbenzenesulfonic acid solution was introduced at a constant rate over 3 hours with stirring in a nitrogen atmosphere, followed by reaction crystallization of sodium p-styrenesulfonate (the sodium hydroxide concentration in the reactor at the start of the reaction was as high as 34.96 wt % and gradually decreased to 17.85 wt % after 3 hours from the start of the reaction (at the end of the reaction), and the p-β-bromoethylbenzenesulfonic acid concentration gradually increased from 0.00 wt % at the start of the reaction to 34.29 wt % after 3 hours from the start of the reaction (at the end of the reaction)). A slurry thereof was cooled to 40° C. over 2 hours. Thereafter, solid-liquid separation was performed by centrifugation, and 980 kg of a wet cake having a sodium styrenesulfonate content of 84.2 wt % was obtained by shaking for 40 minutes. Using a uniaxial screw blender, this wet cake was forcedly fluidized at 40° C. and a rotational speed of 20 rpm for 60 minutes. Sodium p-styrenesulfonate obtained had a median diameter of 22.0 µm, a content of small particles less than 10.00 µm of 12.50 wt %, a water content of 10.2 wt % and a repose angle of 59 degrees. The dissolution time in water was 127 seconds. However, it is clear that this is inferior in fluidity as compared to Example 9 and also has a high water content (the sodium p-styrenesulfonate content is low).

Then, a stainless steel reactor having a jacket and equipped with a stirrer was charged with 1,000 g of the above-mentioned sodium p-styrenesulfonate, 1.0 g of sodium nitrite, 20.0 g of sodium hydroxide and 950.0 g of pure water, followed by stirring at 40° C. for 1 hour under a nitrogen atmosphere. Then, after cooling to room temperature over 3 hours, solid-liquid separation was performed with a centrifuge to obtain 891.0 g of a wet cake of high-purity sodium p-styrenesulfonate.

The above-mentioned sodium p-styrenesulfonate after purification had a purity of 85.5 wt %, a water content of 10.5 wt % and a sodium bromide content of 1.21 wt %. The contents of organic impurities such as isomers were (a) 0.15%, (b) 2.56%, (c) 6.20%, (d) 0.03% and (e) 0.20%.

Incidentally, sodium p-styrenesulfonate before purification had a purity of 84.2 wt %, a water content of 10.2 wt % and a sodium bromide content of 2.20 wt %. The contents of organic impurities such as isomers were (a) 0.41%, (b) 3.21%, (c) 7.12%, (d) 0.05% and (e) 0.70% (provided that the sum of peak areas of sodium p-styrenesulfonate and (a) to (e) is 100). It is therefore clear that the degree of purification is low as compared to Example 9. The reason for this is considered to be that solid-liquid separation did not smoothly proceed because of poor centrifugal filterability.

the like), chemical mechanical polishing (so-called CMP) slurries, photographic silver halides and the like.

DESCRIPTION OF REFERENCE NUMERALS AND SIGNS (a): Absorption peak of sodium o-styrenesulfonate
(b): Absorption peak of sodium p-β-bromoethylbenzenesulfonate
(c): Absorption peak of sodium m-styrenesulfonate

TABLE 2

|  |  | Example 6 | Example 7 | Example 8 | Example 9 | Comparative Example 7 | Comparative Example 8 | Comparative Example 9 |
|---|---|---|---|---|---|---|---|---|
| [Properties and composition before purification] | | | | | | | | |
| Median diameter | μm | 63.1 | 110.0 | 37.0 | The same | 19.8 | 160.0 | 22.0 |
| Small particles less than 10.00 μm | % | 1.5 | 0.0 | 3.1 | as | 13.6 | 0.0 | 12.5 |
| Repose angle | deg | 47 | 43 | 51 | Example | 59 | 45 | 59 |
| Rate of dissolution | sec | 160 | 200 | 140 | 6 | 130 | 270 | 127 |
| Purity | wt % | 88.5 | 88.9 | 88.9 | | 83.4 | 85.1 | 84.2 |
| Water content | wt % | 7.1 | 6.1 | 8.6 | | 10.4 | 5.9 | 10.2 |
| Iron content | μg/g | 0.80 | 0.61 | 0.85 | | 4.93 | 3.21 | 3.18 |
| Sodium bromide | wt % | 2.10 | 1.98 | 2.23 | | 2.10 | 1.84 | 2.20 |
| Organic impurities | %[1)] | | | | | | | |
| (a) Sodium o-styrenesulfonate | | 0.16 | 0.14 | 0.22 | | 0.35 | 0.11 | 0.41 |
| (b) Sodium p-β-bromoethylbenzenesulfonate | | 0.43 | 0.21 | 0.71 | | 3.46 | 0.16 | 3.21 |
| (c) Sodium m-styrenesulfonate | | 2.64 | 2.36 | 3.10 | | 7.74 | 2.21 | 7.12 |
| (d) Sodium bromostyrenesulfonate | | 0.12 | 0.05 | 0.65 | | 0.06 | 0.02 | 0.05 |
| (e) Sodium p-β-hydroxyethylbenzenesulfonate | | 0.48 | 0.17 | 0.53 | | 0.70 | 0.23 | 0.70 |
| [Properties and composition after purification] | | | | | | | | |
| Median diameter | μm | — | — | — | 48.0 | 22.3 | — | 25.1 |
| Small particles less than 10.00 μm | % | — | — | — | 2.5 | 3.1 | — | 1.6 |
| Repose angle | deg | — | — | — | 50 | 58 | — | 58 |
| Rate of dissolution | sec | — | — | — | 130 | 128 | — | 130 |
| Purity | wt % | — | — | — | 89.1 | 85.5 | — | 85.5 |
| Water content | wt % | — | — | — | 8.6 | 10.8 | — | 10.5 |
| Iron content | μg/g | — | — | — | 0.76 | 4.89 | — | 3.15 |
| Sodium bromide | wt % | — | — | — | 0.20 | 1.10 | — | 1.21 |
| Organic impurities | %[1)] | | | | | | | |
| (a) Sodium o-styrenesulfonate | | — | — | — | 0.06 | 0.22 | — | 0.15 |
| (b) Sodium p-β-bromoethylbenzenesulfonate | | — | — | — | 0.03 | 2.80 | — | 2.56 |
| (c) Sodium m-styrenesulfonate | | — | — | — | 1.34 | 6.93 | — | 6.20 |
| (d) Sodium bromostyrenesulfonate | | — | — | — | 0.10 | 0.05 | — | 0.03 |
| (e) Sodium p-β-hydroxyethylbenzenesulfonate | | — | — | — | 0.00 | 0.20 | — | 0.20 |

[1)]The area ratio at the time when the sum of HPLC peak areas of (a) to (e) and sodium p-styrenesulfonate is taken as 100

INDUSTRIAL APPLICABILITY

High-purity sodium p-styrenesulfonate of the present invention improved in hue and Poly(Sodium p-Styrenesulfonate) produced using the same are useful for uses of dispersants for producing pigment dispersions or polymer emulsions, synthetic starch for cleaning of clothing and ironing finishing, personal care products, antistatic agents, flame retardants for transparent resins and the like, because of their excellent hue.

Further, high-purity sodium p-styrenesulfonate of the present invention also has excellent fluidity and solubility, and useful in a wide range of industrial fields, such as reactive emulsifiers for emulsion polymerization, production of dispersants necessary for aqueous dispersions of pigments, antioxidants, various polymers (tackifier resins, chloroprene rubber, polyacrylic acid esters, polyesters, styrene-butadiene copolymers, polyvinyl chloride, silicone polymers, conductive polymers and the like), nanocarbon materials, hot forging release agents (slurries of silica particles or the like), battery electrode materials (carbon, lithium iron phosphate, lithium manganese phosphate and (d): Absorption peak of sodium bromostyrenesulfonate
(e): Absorption peak of sodium p-β-hydroxyethylbenzenesulfonate
NaSS (para form): Absorption peak of sodium p-styrenesulfonate
Elution solvent: Absorption peak derived from an eluent (switched)

The invention claimed is:

1. High-purity sodium p-styrenesulfonate with an excellent hue having an APHA value of a 15 wt % aqueous solution of sodium p-styrenesulfonate and poly(sodium p-styrenesulfonate)≤100, in which the iron content in sodium p-styrenesulfonate is less than 3.00 μg/g, the sodium bromide content is less than 2.50 wt %, and the peak area ratios of (a) sodium o-styrenesulfonate, (b) sodium p-β-bromoethylbenzenesulfonate, (c) sodium m-styrenesulfonate, (d) sodium bromostyrenesulfonate and (e) sodium p-β-hydroxyethylbenzenesulfonate, which are determined by high-performance liquid chromatography (HPLC), are (a) ≤0.40%, (b) ≤4.00%, (c) ≤8.00%, (d) ≤0.10% and (e) ≤0.80%, respectively (provided that the sum of peak areas of sodium p-styrenesulfonate and (a) to (e) is 100).

2. High-purity sodium p-styrenesulfonate with an excellent hue having an APHA value of a 15 wt % aqueous solution of sodium p-styrenesulfonate and poly(sodium p-styrenesulfonate)≤100 according to claim 1, wherein the iron content in sodium p-styrenesulfonate is less than 3.00 μg/g, the sodium bromide content is less than 2.50 wt %, and the peak area ratios of (a) sodium o-styrenesulfonate, (b) sodium p-β-bromoethylbenzenesulfonate, (c) sodium m-styrenesulfonate, (d) sodium bromostyrenesulfonate and (e) sodium p-β-hydroxyethylbenzenesulfonate, which are determined by high-performance liquid chromatography (HPLC), are (a) ≤0.20%, (b) ≤0.50%, (c) ≤3.00%, (d) ≤0.10% and (e) ≤0.20%, respectively (provided that the sum of peak areas of sodium p-styrenesulfonate and (a) to (e) is 100).

3. High-purity sodium p-styrenesulfonate with an excellent hue having an APHA value of a 15 wt % aqueous solution of sodium p-styrenesulfonate and poly(sodium p-styrenesulfonate)≤100 according to claim 1, which is composed of particles having a median diameter measured with a laser diffraction/scattering particle size analyzer of 25.00 to 150.00 μm and a content of small particles less than 10.00 μm of 10.00% or less, and has a water content of 10.00 wt % or less and a repose angle of 55 degrees or less.

4. High-purity sodium p-styrenesulfonate with an excellent hue having an APHA value of a 15 wt % aqueous solution of sodium p-styrenesulfonate and poly(sodium p-styrenesulfonate)≤100 according to claim 3, which is composed of particles having a median diameter measured with a laser diffraction/scattering particle size analyzer of 40.00 to 90.00 μm and a content of small particles less than 10.00 μm of 3.00% or less, and has a water content of 8.00 wt % or less and a repose angle of 50 degrees or less.

5. High-purity sodium p-styrenesulfonate with an excellent hue having an APHA value of a 15 wt % aqueous solution of sodium p-styrenesulfonate and poly(sodium p-styrenesulfonate)≤100 according to claim 1, wherein the sodium bromide content is 0.20 wt % or less.

6. A method for producing high-purity sodium p-styrenesulfonate with an excellent hue according to claim 1 comprising concurrently feeding sodium hydroxide and p-β-bromoethyl-benzenesulfonic acid to a reaction tank at a constant rate, wherein reaction crystallization is performed at 60 to 110° C. for 1 to 7 hours, while controlling so as to keep the sodium hydroxide concentration in the reaction tank [(the weight of total sodium hydroxide fed/the weight of the total reaction solution in the reaction tank)×100] at 10.00 to 20.00 wt % and so as to increase the p-β-bromoethyl-benzenesulfonic acid concentration [(the weight of total p-β-bromoethylbenzenesulfonic acid fed/the weight of the total reaction solution in the reaction tank)×100] from 0.00 wt % to 30.00 to 50.00 wt % over 1 to 7 hours, and a wet cake obtained by solid-liquid separation is forcedly fluidized.

7. Poly(sodium p-styrenesulfonate) with an excellent hue having the following repeating structural unit A or the following repeating structural unit A and the following repeating structural unit B, which is produced using high-purity sodium p-styrenesulfonate according to claim 1.

[Chemical Formula 1]

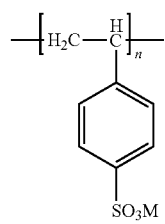

A

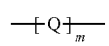

B

[in the repeating structural units A and B, M represents a sodium cation, Q represents a radical polymerizable monomer residue, n represents an integer of 1 or more, and m represents an integer of 0 or more].

8. Poly(sodium p-styrenesulfonate) with an excellent hue according to claim 7, wherein the weight average molecular weight determined by gel permeation chromatography is from 2,000 to 1,000,000.

9. Poly(sodium p-styrenesulfonate) with an excellent hue according to claim 7, wherein Q is a radical polymerizable monomer residue that is one or a combination of two or more kinds selected from the group consisting of a (meth) acrylic acid residue, a (meth)acrylic acid ester residue, a (meth)acrylamide residue, a maleic anhydride residue, a maleic acid residue, an N-phenylmaleimide residue, an N-cyclohexyl-maleimide residue, a styrene residue and a styrene derivative residue.

10. A dispersant comprising poly(sodium p-styrene-sulfonate) with an excellent hue according to claim 7 as an effective ingredient.

11. An ironing agent for clothing produced using poly(sodium p-styrenesulfonate) with an excellent hue according to claim 7 as synthetic starch.

* * * * *